(12) United States Patent
Liston

(10) Patent No.: US 11,806,146 B2
(45) Date of Patent: Nov. 7, 2023

(54) SYSTEMS AND METHODS FOR IDENTIFYING A NEUROPHYSIOLOGICAL BIOTYPE OF DEPRESSION IN THE BRAIN OF A PATIENT

(71) Applicant: Cornell University, Ithaca, NY (US)

(72) Inventor: Conor Liston, New York, NY (US)

(73) Assignee: Cornell University, Ithaca, NY (US)

( * ) Notice: Subject to any disclaimer, the term of this patent is extended or adjusted under 35 U.S.C. 154(b) by 578 days.

(21) Appl. No.: 16/464,191

(22) PCT Filed: Nov. 28, 2017

(86) PCT No.: PCT/US2017/063425
§ 371 (c)(1),
(2) Date: May 24, 2019

(87) PCT Pub. No.: WO2018/098467
PCT Pub. Date: May 31, 2018

(65) Prior Publication Data
US 2020/0289044 A1    Sep. 17, 2020

Related U.S. Application Data

(60) Provisional application No. 62/426,835, filed on Nov. 28, 2016.

(51) Int. Cl.
*A61B 5/16* (2006.01)
*G16H 50/70* (2018.01)
(Continued)

(52) U.S. Cl.
CPC ............ *A61B 5/165* (2013.01); *A61B 5/0042* (2013.01); *A61B 5/055* (2013.01); *A61B 5/4848* (2013.01);
(Continued)

(58) Field of Classification Search
None
See application file for complete search history.

(56) References Cited

U.S. PATENT DOCUMENTS

2016/0019693 A1*  1/2016  Silbersweig .......... G06T 11/206
                                                              382/128
2017/0343634 A1* 11/2017  Lencz .................. A61B 5/0042

OTHER PUBLICATIONS

Cao et al., "Aberrant functional connectivity for diagnosis of major depressive disorder: A discriminant analysis", Psychiatry and Clinical Neurosciences 2014; 68: 110-119. (Year: 2014).*
(Continued)

*Primary Examiner* — Yi-Shan Yang
(74) *Attorney, Agent, or Firm* — McDermott Will & Emery LLP

(57) ABSTRACT

The methods and systems described herein enable the accurate diagnosis of novel biotypes of depression that transcend current diagnostic boundaries and may be useful for identifying individuals who are most likely to benefit from antidepressant treatment. Functional magnetic resonance imaging is used to characterize the architecture of functional connectivity across the brain to show that patients with depression can be subdivided into four neurophysiological biotypes based solely on unique patterns of abnormal connectivity in resting state brain networks. Clustering subjects on this basis reduces diagnostic heterogeneity, enabling the development of depression biotype classifiers for diagnosing biotypes of depresion in individual patients, These biotypes also predict differing responses to antidepressant treatment, and abnormal connectivity patterns can be used to track changes in depression severity over time.

21 Claims, 7 Drawing Sheets

(51) Int. Cl.
G16H 50/20 (2018.01)
G16H 20/70 (2018.01)
A61B 5/00 (2006.01)
A61B 5/055 (2006.01)
G01R 33/48 (2006.01)
G01R 33/56 (2006.01)
A61N 2/00 (2006.01)

(52) U.S. Cl.
CPC .......... A61B 5/7264 (2013.01); A61B 5/7275 (2013.01); G01R 33/4806 (2013.01); G01R 33/5608 (2013.01); G16H 20/70 (2018.01); G16H 50/20 (2018.01); G16H 50/70 (2018.01); A61N 2/006 (2013.01)

(56) References Cited

OTHER PUBLICATIONS

Bakker, "Resting-state functional connectivity predicts individual treatment outcomes of repetitive transcranial magnetic stimulation for major depression disorder", Institute of Medical Science, University of Toronto, 2014. (Year: 2014).*

Guo et al., "Distinct neurobiological signatures of brain connectivity in depression subtypes during natural viewing of emotionally salient films", Psychological Medicine, vol. 46, Issue 7, May 2016, pp. 1535-1545 (pp. 1-11). Cambridge University Press 2016. (Year: 2016).*

International Search Report and Written Opinion dated Mar. 9, 2018 in PCT Application No. PCT/US2017/063425.

Bakker, Nathan. "Resting-State Functional Connectivity Predicts Individual Treatment Outcomes of Repetitive Transcranial Magnetic Stimulation for Major Depressive Disorder" Jan. 1, 2014. Retrieved from the Internet: URL: https://search.proquest.com/docview/1771278068?accountid=29404.

Cao, Longlong, et al. "Aberrant functional connectivity for diagnosis of major depressive disorder: A discriminant analysis: Potential new biomarkers for MDD" Psychiatry and Clinical Neurosciences, vol. 68, No. 2, pp. 110-119, Oct. 31, 2013.

Grotegerd, Dominik, et al. "Discriminating unipolar and bipolar depression by means of fMRI and pattern classification: a pilot study", European Archives of Psychiatry and Clinical Neuroscience, vol. 263, No. 2, pp. 119-131, May 26, 2012.

Liberg, Benny, et al. "Functional and structural alterations in the cingulate motor area relate to decreased fronto-striatal coupling in major depressive disorder with psychomotor disturbances" Frontiers in Psychiatry, vol. 5, Dec. 4, 2014.

Liston, Conor, et al. "Default Mode Network Mechanisms of Transcranial Magnetic Stimulation in Depression", Biological Psychiatry, vol. 76, No. 7, pp. 517-526, Oct. 1, 2014.

Lord, Anton, et al. "Changes in Community Structure of Resting State Functional Connectivity in Unipolar Depression" PLOS ONE, vol. 7, No. 8, p. e41282, Aug. 20, 2012.

Oathes, Desmond J., et al. "Neurobiological signatures of anxiety and depression in resting-state fMRI" Biol. Psychiatry, vol. 77, No. 4, pp. 385-393, Feb. 15, 2015.

Rajamannar, Ramasubbu, et al. "Accuracy of automated classification of major depressive disorder as a function of symptom severity" Neuroimage: Clinical, vol. 12, pp. 320-331, Feb. 1, 2016.

Rashid, Barnaly, et al. "Classification of schizophrenia and bipolar patients using static and dynamic resting-state fMRI brain connectivity" Neuroimage, vol. 134, pp. 645-657, Jul. 1, 2016.

Veloso, Telma Alves. "Exploration and application of machine learning algorithms to functional connectivity data" Jan. 1, 2014 Retrieved from the Internet: URL: https://repositorium.sdum.uminho.pt/bitstream/1822/34155/1/Telma%20Alves%20Veloso.pdf.

Wei, Maobin et al. "Identifying major depressive disorder using Hurst exponent of resting-state brain networks" Psychiatry Research: Neuroimaging, vol. 214, No. 3, pp. 306-312, 2013.

Williams, Leanne M. "Defining biotypes for depression and anxiety based on large-scale circuit dysfunction: a theoretical review of the evidence and future directions for clinical translation" Depress Anxiety, vol. 34, No. 1, pp. 9-24, Jan. 2017.

Office Action dated Jul. 1, 2022 in European Patent Application No. 17822091.9. A.

Williams LM. Defining biotypes for depression and anxiety based on large-scale circuit dysfunction: a theoretical review of the evidence and future directions for clinical translation. Depress Anxiety. Jan. 2017;34(1):9-24. doi: 10.1002/da.22556. Epub Sep. 21, 2016. PMID: 27653321; PMCID: PMC5702265.

* cited by examiner

SYSTEMS AND METHODS FOR IDENTIFYING A NEUROPHYSIOLOGICAL BIOTYPE OF DEPRESSION IN THE BRAIN OF A PATIENT

RELATED APPLICATIONS

The present application is a United States National Phase under 35 U.S.C. § 371 of International Application No. PCT/US2017/063425, filed on Nov. 28, 2017, which claims priority to, and the benefit of, U.S. Provisional Patent Application No. 62/426,835, entitled "NEUROIMAGING BIOMARKERS FOR DIAGNOSING DEPRESSION SUBTYPES AND PREDICTING AND QUANTIFYING TREATMENT RESPONSE" and filed on Nov. 28, 2016, the entire contents of both of which are hereby incorporated by reference for all purposes.

BACKGROUND

Depression diagnosis continues to be a challenge for physicians and psychiatrists. Experts have concerns over the traditional subjective clinical symptom approach to depression diagnosis, especially for diagnosing depression biotypes. More objective measures are needed to detect a subject's depression and predict their treatment response.

SUMMARY

According to one aspect, the disclosure relates to a method for a classifying neurophysiological biotype of depression in the brain of a patient. The method includes receiving, by a processor, fMRI data indicative of brain activity of a patient and extracting, by the processor, brain region functional connectivity information from the fMRI signal. The method also includes identifying a depression biotype for the patient by applying a biotype classifier executing on the processor to the brain region functional connectivity information extracted from the fMRI signal and outputting, by the processor, the identified depression biotype.

In some implementations, the biotype classifier may include a plurality of classifiers. The plurality of classifiers may include a first set of classifiers, where each classifier is configured to generate a biotype depression likelihood score for a different corresponding depression biotype. The depression biotype is identified by selecting the depression biotype associated with the classifier that generates the highest biotype depression likelihood score based on the extracted brain region functional connectivity information. In some implementations, the extracted brain region functional connectivity information includes functional connectivity levels between a plurality of the following patient brain regions: the dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex.

In some implementations, the method may include processing the extracted brain functional connectivity information by an additional classifier included in a second set of classifiers configured for determining if the patient suffers from depression, wherein the additional classifier is associated with the depression biotype identified for the patient.

In some implementations, determining if the patient suffers from a first biotype of depression or if the patient has no known depression diagnosis, includes processing the extracted brain region functional connectivity information between a plurality of the following patient brain regions: the posterior parietal cortex, precuneus, middle temporal gyrus, parahippocampal cortex, dorsolateral prefrontal cortex, ventrolateral prefrontal cortex, insular cortex, temporal pol, superior temporal gyms, ventromedial prefrontal cortex, ventral hippocampus, amygdala, ventral caudate nucleus, ventral striatum, thalamus, primary somatosensory cortex, primary motor cortex, visual cortex.

In some implementations, determining if the patient suffers from a second biotype or if the patient has no known depression diagnosis, includes processing the extracted brain region functional connectivity information between a plurality of the following patient brain regions: the dorsomedial prefrontal cortex, ventromedial prefrontal cortex, orbitofrontal cortex, posterior cingulate cortex, fusiform gyms, middle temporal gyrus, parahippocampal cortex, anterior cingulate cortex, ventrolateral prefrontal cortex, dorsolateral prefrontal cortex, insular cortex, posterior parietal cortex, thalamus, primary somatosensory cortex, primary motor cortex, and visual cortex.

In some implementations, determining if the patient suffers from a third biotype of depression or if the patient has no known depression diagnosis, includes processing the extracted brain region functional connectivity information between a plurality of the following patient brain regions: the ventromedial prefrontal cortex, posterior parietal cortex, middle temporal gyms, parahippocampal cortex, ventrolateral prefrontal cortex, anterior prefrontal cortex, dorsolateral prefrontal cortex, posterior parietal cortex, temporal pole, superior temporal gyrus, orbitofrontal cortex, ventral hippocampus, amygdala, subgenual anterior cingulate cortex, ventral caudate nucleus, ventral striatum, thalamus, premotor cortex, supplementary motor area, insular cortex, anterior cingulate cortex, and fusiform gyrus.

In some implementations, determining if the patient suffers from a fourth biotype of depression or if the patient has no known depression diagnosis, processing the extracted brain region functional connectivity information between a plurality of the following patient brain regions: the fusiform gyrus, parahippocampal cortex, ventrolateral prefrontal cortex, posterior parietal cortex, anterior cingulate cortex, middle cingulate cortex, insular cortex, temporal pole, superior temporal gyms, middle temporal gyrus, orbitofrontal cortex, ventral hippocampus, subgenual anterior cingulate cortex, ventral striatum, thalamus, primary somatosensory cortex, supplementary motor area, insular cortex, postcentral gyms, and lingual gyrus.

In some implementations, the biotype classifier may include a linear support vector machine classifier configured to output the likelihood of an associated depression biotype. In some implementations, the method for identifying the depression biotype may include a principal component analysis of the brain region functional connectivity extracted from the fMRI signal.

In some implementations, the method may also include classifying a depression treatment prognosis for the patient by applying a prognosis classifier to the extracted brain region functional connectivity information, wherein the prognosis classifier outputs a likelihood of success of an identified depression treatment for the patient. In some implementations, likelihood of success of an identified depression treatment for the patient includes processing the extracted brain region functional connectivity information between a plurality of the following patient brain regions: the dorsomedial prefrontal cortex, anterior cingulate cortex, posterior cingulate cortex, ventromedial prefrontal cortex, ventrolateral prefrontal cortex, dorsolateral prefrontal cortex, posterior parietal cortex, orbitofrontal cortex, amygdala, ventral striatum, nucleus accumbens, globus pallidus, thalamus, primary motor cortex, primary somatosensory cortex, and visual cortex. In some implementations, the identified depression biotype comprises a principal component analysis of the brain region functional connectivity extracted from the fMRI signal. In some implementations, the depression treatment is a repetitive transcranial magnetic stimulation.

In some implementations, the method may also predict a depression severity of the patient by processing the extracted brain region functional connectivity information with a multiple linear regression model. In some implementations, predicting the depression severity for a patient comprises processing the extracted brain region functional connectivity information between a plurality of the following patient brain regions: the dorsomedial prefrontal cortex, posterior cingulate cortex, precuneus, posterior parietal cortex, middle temporal gyrus, parahippocampal cortex, anterior prefrontal cortex, anterior cingulate cortex, ventrolateral prefrontal cortex, insular cortex, orbitofrontal cortex, ventral hippocampus, ventral striatum, thalamus, primary motor cortex, premotor cortex, and visual cortex.

According to one aspect, the disclosure relates to a system for classifying neurophysiological biotypes of depression in the brain of a patient. The system may include an input module configured to receive fMRI data from an fMRI scan. In some implementations, an fMRI machine may be coupled to the input module. The system may also include a connectivity evaluation module configured to process the received fMRI data to extract brain region functional connectivity information associated with a brain of the patient. The system may also include a classification module configured to classify the patient into one of a plurality of depression biotypes and an output module for outputting the depression biotype into which the patient was classified.

In some implementations, the system may also include a biotype classification module. The biotype classification module may include a plurality of classifiers, including a first set of classifiers, where each classifier configured to generate a biotype depression likelihood score for a different depression biotype. The depression biotype is identified by selecting the depression biotype associated with the classifier that generates the highest biotype depression likelihood score based on the extracted brain region functional connectivity information. In some implementations, the extracted brain region functional connectivity information comprises functional connectivity levels between a plurality of the following patient brain regions: the dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex.

In some implementations, the biotype classification module may be configured to process the extracted brain functional connectivity information by an additional classifier included in a second set of classifiers. The second set of classifiers may be configured to determine if the patient suffers from depression, and associated with the depression biotype identified for the patient.

In some implementations, the biotype classification module may be configured to determine if the patient suffers from a first biotype of depression or if the patient has no known depression diagnosis, by processing the extracted brain region functional connectivity information between a plurality of the following patient brain regions: the posterior parietal cortex, precuneus, middle temporal gyrus, parahippocampal cortex, dorsolateral prefrontal cortex, ventrolateral prefrontal cortex, insular cortex, temporal pol, superior temporal gyrus, ventromedial prefrontal cortex, ventral hippocampus, amygdala, ventral caudate nucleus, ventral striatum, thalamus, primary somatosensory cortex, primary motor cortex, visual cortex.

In some implementations, the biotype classification module may be configured to determine if the patient suffers from a second biotype of depression or if the patient has no known depression diagnosis, by processing the extracted brain region functional connectivity information between a plurality of the following patient brain regions: the dorsomedial prefrontal cortex, ventromedial prefrontal cortex, orbitofrontal cortex, posterior cingulate cortex, fusiform gyrus, middle temporal gyrus, parahippocampal cortex, anterior cingulate cortex, ventrolateral prefrontal cortex, dorsolateral prefrontal cortex, insular cortex, posterior parietal cortex, thalamus, primary somatosensory cortex, primary motor cortex, and visual cortex.

In some implementations, the biotype classification module may be configured to determine if the patient suffers from a third biotype of depression or if the patient has no known depression diagnosis, by processing the extracted brain region functional connectivity information between a plurality of the following patient brain regions: the ventromedial prefrontal cortex, posterior parietal cortex, middle temporal gyrus, parahippocampal cortex, ventrolateral prefrontal cortex, anterior prefrontal cortex, dorsolateral prefrontal cortex, posterior parietal cortex, temporal pole, superior temporal gyrus, orbitofrontal cortex, parahippocampal cortex, ventral hippocampus, amygdala, subgenual anterior cingulate cortex, ventral caudate nucleus, ventral striatum, thalamus, premotor cortex, supplementary motor area, insular cortex, anterior cingulate cortex, and fusiform gyrus.

In some implementations, the biotype classification module may be configured to determine if the patient suffers from a fourth biotype of depression or if the patient has no known depression diagnosis, by processing the extracted brain region functional connectivity information between a plurality of the following patient brain regions: the fusiform gyrus, parahippocampal cortex, ventrolateral prefrontal cortex, posterior parietal cortex, anterior cingulate cortex, middle cingulate cortex, insular cortex, temporal pole, superior temporal gyrus, middle temporal gyrus, orbitofrontal cortex, ventral hippocampus, subgenual anterior cingulate cortex, ventral striatum, thalamus, primary somatosensory cortex, supplementary motor area, insular cortex, postcentral gyrus, and lingual gyrus.

In some implementations, the biotype classification module may be configured to identify the identified depression biotype with a principal component analysis of the brain region functional connectivity extracted from the fMRI signal. In some implementations, the biotype classification module may include a linear support vector machine classifier configured to output the likelihood of an associated depression biotype.

In some implementations, the system may also include a depression treatment prognosis classifier for the patient configured to apply a prognosis classifier to the extracted brain region functional connectivity information. The prognosis classifier is configured to output a likelihood of success of an identified depression treatment for the patient. In some implementations, the depression treatment prognosis classifier may be configured to identify the likelihood of success of an identified depression treatment for the patient by processing the extracted brain region functional connectivity information between a plurality of the following patient brain regions: the dorsomedial prefrontal cortex, anterior cingulate cortex, posterior cingulate cortex, ventromedial prefrontal cortex, ventrolateral prefrontal cortex, dorsolateral prefrontal cortex, posterior parietal cortex, orbitofrontal cortex, amygdala, ventral striatum, nucleus accumbens, globus pallidus, thalamus, primary motor cortex, primary somatosensory cortex, and visual cortex.

In some implementations, the depression treatment prognosis classifier may be configured to identify the likelihood of success of an identified depression treatment for the patient based on a principal component analysis of the brain region functional connectivity extracted from the fMRI signal. In some implementations, the identified depression treatment is a repetitive transcranial magnetic stimulation.

In some implementations, the system may also include a depression severity predictor configured to predict a depression severity of the patient by processing the extracted brain region functional connectivity information with a multiple linear regression model. In some implementations, the depression severity predictor may be configured to predict the depression severity for a patient by processing the extracted brain region functional connectivity information between a plurality of the following patient brain regions: the dorsomedial prefrontal cortex, posterior cingulate cortex, precuneus, posterior parietal cortex, middle temporal gyrus, parahippocampal cortex, anterior prefrontal cortex, anterior cingulate cortex, ventrolateral prefrontal cortex, insular cortex, orbitofrontal cortex, ventral hippocampus, ventral striatum, thalamus, primary motor cortex, premotor cortex, and visual cortex.

According to one aspect, the disclosure relates to a non-transitory computer readable medium storing a computer readable instructions, which when executed by a processor cause the processor to carry out a method for classifying biotypes of depression. The method includes receiving, by the processor, fMRI data indicative of brain activity of a patient and extracting, by the processor, brain region functional connectivity information from the fMRI signal. The method also includes identifying a depression biotype for the patient by applying a biotype classifier executing on the processor to the brain region functional connectivity information extracted from the fMRI signal and outputting, by the processor, the identified depression biotype.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION OF THE DRAWINGS

The various concepts introduced above and discussed in greater detail below may be implemented in various ways, as the described concepts are not limited to any particular manner of implementation. Examples of specific implementations are provided for illustrative purposes.

Depression is a heterogeneous clinical syndrome linked to dysfunction and abnormal connectivity in frontostiatal and limbic networks of the brain. Depression is typically diagnosed when a patient suffers from at least five of nine symptoms—allowing for several hundred unique combinations of changes in mood, appetite, sleep, energy, cognition, and motor activity. Diagnostic heterogeneity has emerged as a major obstacle to understanding the pathophysiology of major mental illnesses and depression. Although major depressive disorders, especially highly recurrent depression, is up to 45% heritable, identifying genetic risk factors has proven challenging, even in extremely large genome-wide association studies. Likewise, efforts to develop new treatments have slowed, due in part to a lack of physiological targets for assessing treatment efficacy and selecting individual patients who are most likely to benefit. All of these challenges have been attributed in part to the fact that our current diagnostic system assigns a single label to a syndrome that is not unitary and may be caused by distinct pathological processes requiring different treatments.

The present system and methods described herein diagnose and predict treatment responses for patients suffering with depression by classifying the patient into a depression biotype based on unique patterns of abnormal connectivity in brain networks, including resting state brain networks. Functional connectivity may reflect the relationship between neuronal activation patterns in two or more regions of the brain over time evaluated by a functional magnetic resonance imaging or functional MRI (fMRI).

Figure 1:
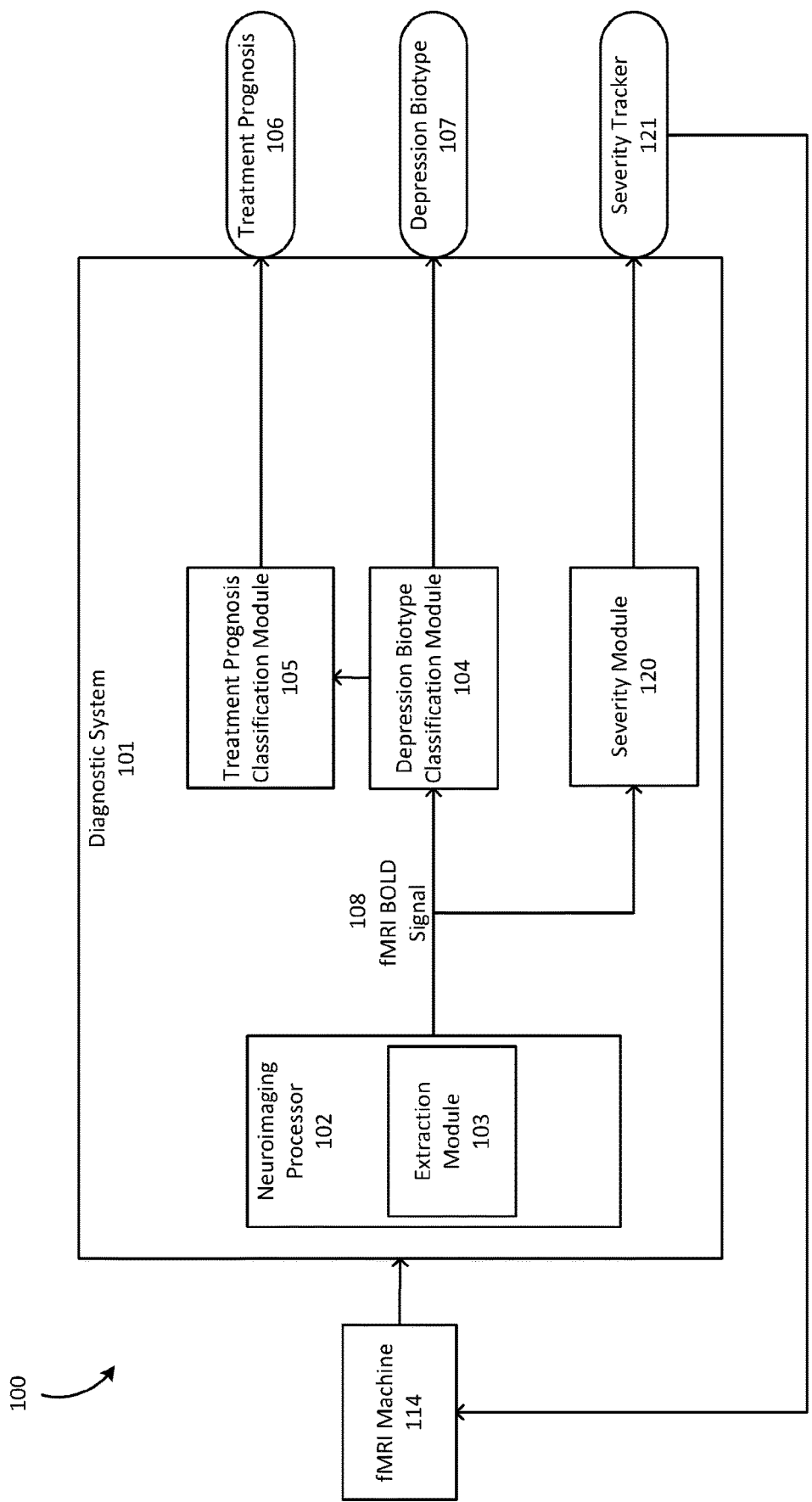
FIG. 1 illustrates a first schematic diagram of an example diagnostic system for classifying a subject into a depression biotype and predicting a treatment prognosis.

FIG. 1 illustrates an example block diagram of the system 100 for diagnosing depression biotypes in the brain and predicting treatment responses. The system 100 includes a diagnostic system 101, which includes a neuroimaging processor 102, depression biotype classification module 104, a treatment prognosis classification module 105, and a severity module 120. The diagnostic system 101 receives fMRI data from a subject undergoing an fMRI in an fMRI machine 114.

Figure 3:
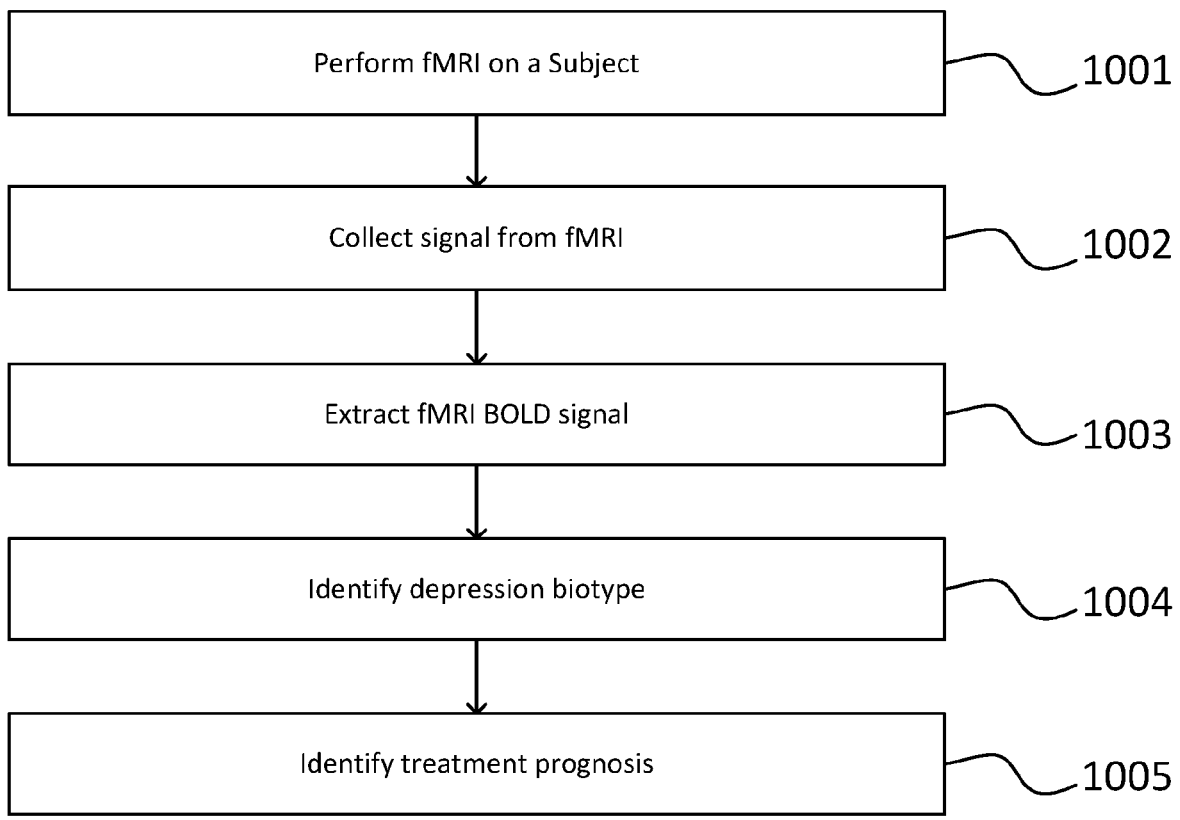
FIG. 3 illustrates a flow chart of an example method for identifying depression biotypes in a subject.

The system 100 includes a diagnostic system 101. The diagnostic system 101 collects fMRI data from an fMRI machine 114. The fMRI machine 114 uses magnetic resonance imaging to map neural networks of a subject's brain and records in vivo a whole brain scan of an individual. The neuroimaging processor 102 processes fMRI data. In some implementations, the neuroimaging processor will process the fMRI data to control for motion, age, and scanner related effects, or any combination thereof. The neuroimaging processor 102 includes an extraction module 103. The extraction module 103 extracts the fMRI BOLD signal 108 from the fMRI data. The fMRI BOLD signal includes brain region functional connectivity information. Details of a method for extracting the fMRI BOLD signal are described further in relation to FIG. 3.

The diagnostic system 101 also includes a depression biotype classification module 104. As mentioned above, the extraction module 103 extracts the fMRI BOLD signal 108 from the fMRI data. The depression biotype classification module 104 receives the fMRI BOLD signal 108 from the neuroimaging processor 102 and extraction module 103. The depression biotype classification module 104 then identifies a depression biotype 107 of the subject. The identified depression biotype includes one of at least four depression biotypes, Biotype 1, Biotype 2, Biotype 3, and Biotype 4. A depression biotype is identified based on patterns of abnormal connectivity in resting state brain networks. Details of a method for identifying depression biotypes and details on the alterations in functional connectivity between different brain regions for identifying depression biotypes are described further in relation to FIG. 4.

The diagnostic system 110 also includes a severity module 120. The severity module 120 receives the fMRI BOLD signal from the neuroimaging processor 102 and the extraction module 103. The severity module 120 predicts depression severity based on the pairwise fMRI functional connectivity measures. The severity module 120 outputs a predicted severity score to the severity tracker 121. The severity tracker 121 monitors the subject's predicted depression severity over time based on multiple fMRI scans. Details of a method for predicting a subject's depression severity are described further in relation to FIG. 6.

The diagnostic system 101 also includes a treatment prognosis classification module 105. The treatment prognosis classification module 105 receives the identified depression biotype from the depression biotype classification module 104 and predicts a treatment response based on the subject's depression biotype. The treatment prognosis classification module 105 outputs a treatment prognosis 106. The treatment prognosis 106 informs the subject or their clinician of the likelihood of success of an identified depressive treatment based on their diagnosed depression biotype. Subjects may be differentially responsive to anti-depressant treatment based on their depression biotypes. Some depression biotypes may exhibit very little treatment response to a particular treatment, while other biotypes may exhibit significant treatment response. In some implementations, the treatment may be repetitive transcranial magnetic stimulation (rTMS) targeting the dorsomedial prefrontal cortex for depression. rTMS is a non-invasive neurostimulation treatment for medication resistant depression. Details of a method for identifying treatment response are described further in relation to FIG. 5.

The analysis of the subject's fMRI data may be provided by a computer and outputted by the computer. Details describing the methods of the computer system are described further in FIG. 7 below.

Figure 2:
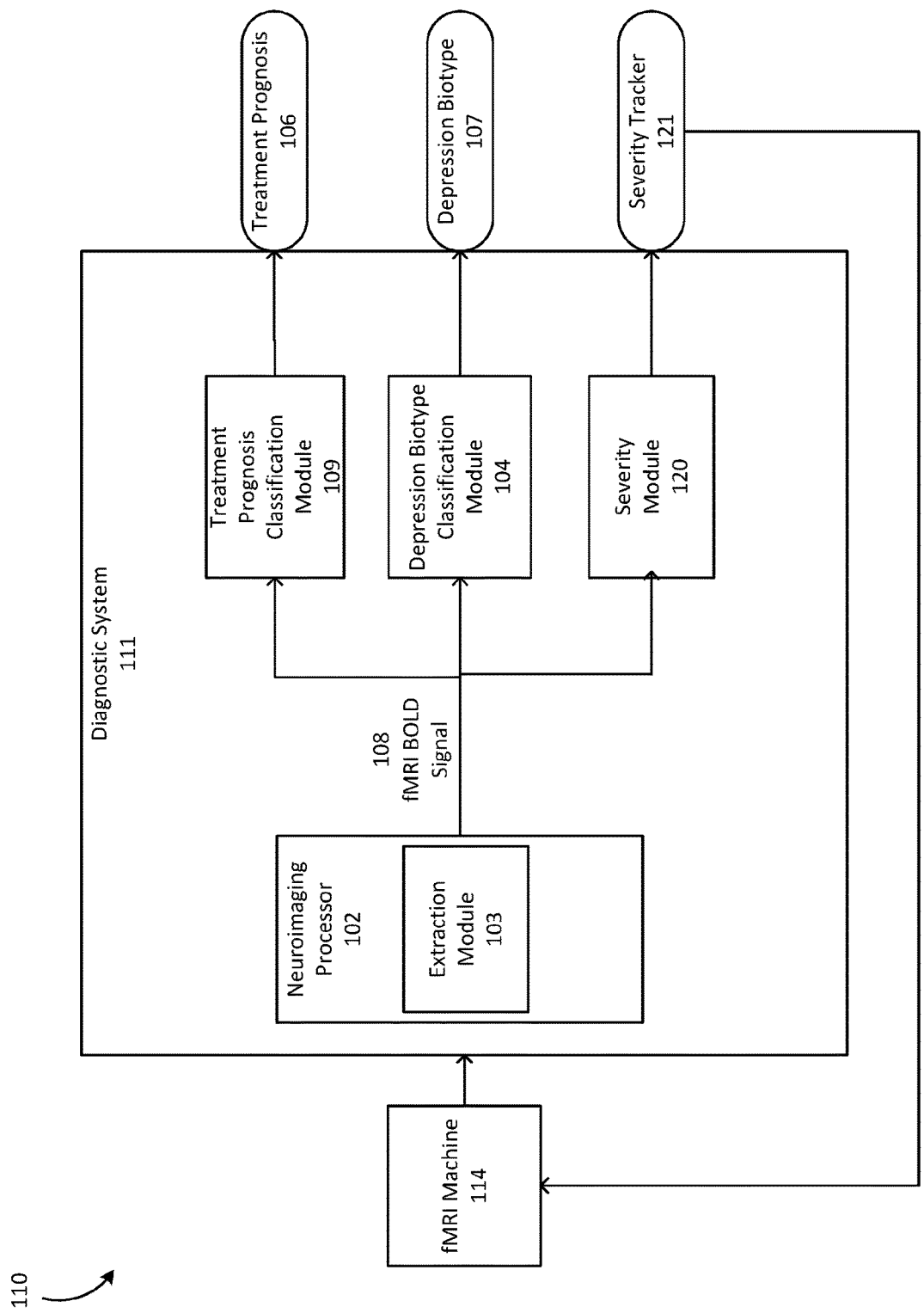
FIG. 2 illustrates a second schematic diagram of an example diagnostic system for classifying a subject into a depression biotype and predicting a treatment prognosis.

FIG. 2 illustrates an example block diagram of a system 110 for identifying depression biotypes in the brain and predicting treatment responses. The system 110 includes a diagnostic system 111. The diagnostic system 111 includes a neuroimaging processor 102, a depression biotype classification module 104, a severity module 120, and a treatment prognosis classification module 109. The diagnostic system receives fMRI data from a subject undergoing an fMRI from an fMRI machine 114.

The system 110 includes a diagnostic system 111. The diagnostic system 111 includes the neuroimaging processor 102. The diagnostic system 111 collects fMRI data from an fMRI machine 114. The neuroimaging processor 102 processes the fMRI data. As mentioned above, in some implementations, the neuroimaging processor will process the data to control for age, motion, and scanner related effects in order to control for artifacts. The neuroimaging processor 102 includes an extraction module 103. The extraction module 103 extracts the fMRI BOLD signal 108 from the fMRI data. Details of a method for extracting the fMRI BOLD signal are described further in relation to FIG. 3.

The diagnostic system 111 also includes a treatment prognosis classification module 109 and a depression biotype classification module 104. The neuroimaging processor 102 outputs the fMRI BOLD signal 108 to the depression biotype classification module 104. The depression biotype classification module 104 outputs the identified depression biotype 107. The depression biotype 107 represents an identified depression biotype determined based on the abnormal functional connectivity in the subject's brain. The depression biotype can be one of a plurality of depression biotypes. Details of a method for identifying depression biotypes and details on the alterations in functional connectivity between different brain regions for identifying depression biotypes are described further in relation to FIG. 4.

The neuroimaging processor 102 also outputs the fMRI BOLD signal 108 to the treatment prognosis classification module 109. The treatment prognosis classifier processes the fMRI BOLD signal 108 and outputs a treatment prognosis 106. The treatment prognosis predicts the anti-depressant treatment response, of the subject, based on their unique fMRI BOLD data. In some implementations, the treatment may be a non-invasive neurostimulation treatment for medication resistant depression, such as rTMS. A more detailed discussion of methods for classifying a subject's response to a depression treatment option as carried out by the treatment prognosis classifier are described in relation to FIG. 5.

The diagnostic system 110 also includes a severity module 120. The severity module 120 receives the fMRI BOLD signal 108 from the neuroimaging processor 102 and the extraction module 103. The severity module 120 outputs a predicted depression severity score, based on the pairwise fMRI functional connectivity measures between different brain regions, to the severity tracker 121. The severity tracker 121 monitors the subject's predicted depression severity over time based on multiple fMRI scans. Details of a method for classifying a subject's depression severity are described further in relation to FIG. 6.

The analysis of the subject's fMRI data may be provided by a computer and outputted by the computer. Details describing the methods of the computer system are described further in FIG. 7 below.

Figure 6:
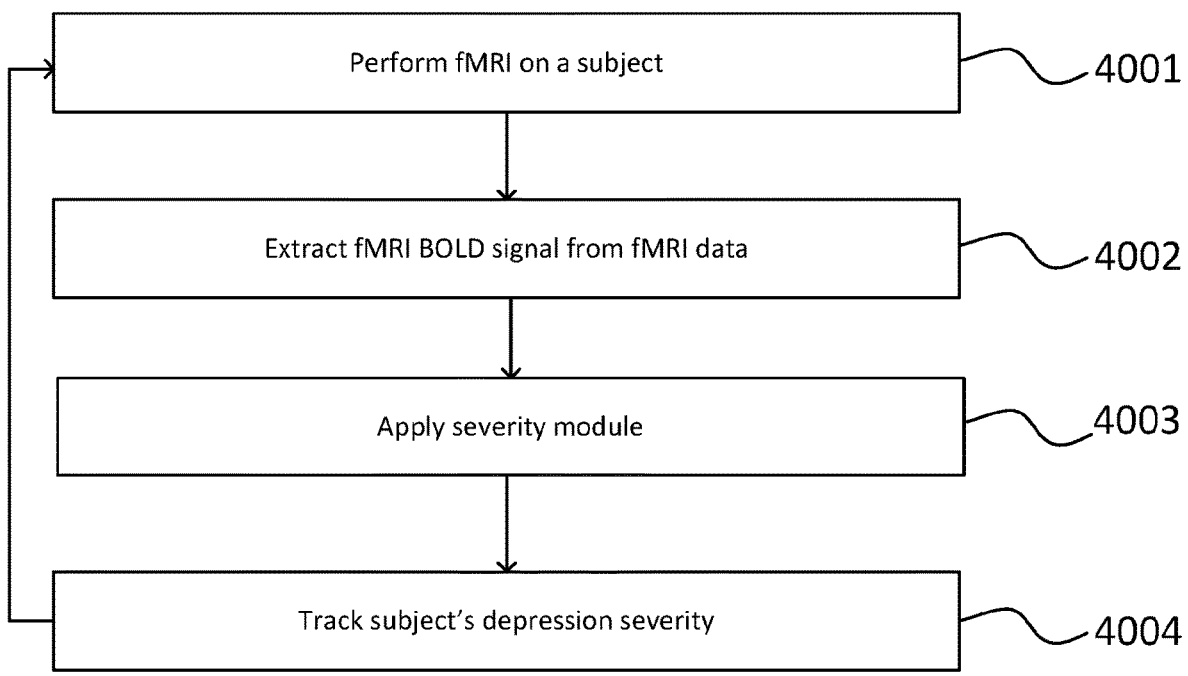
FIG. 6 illustrates a flow chart of an example method for predicting a subject's depression severity and tracking it over time.
Figure 7:
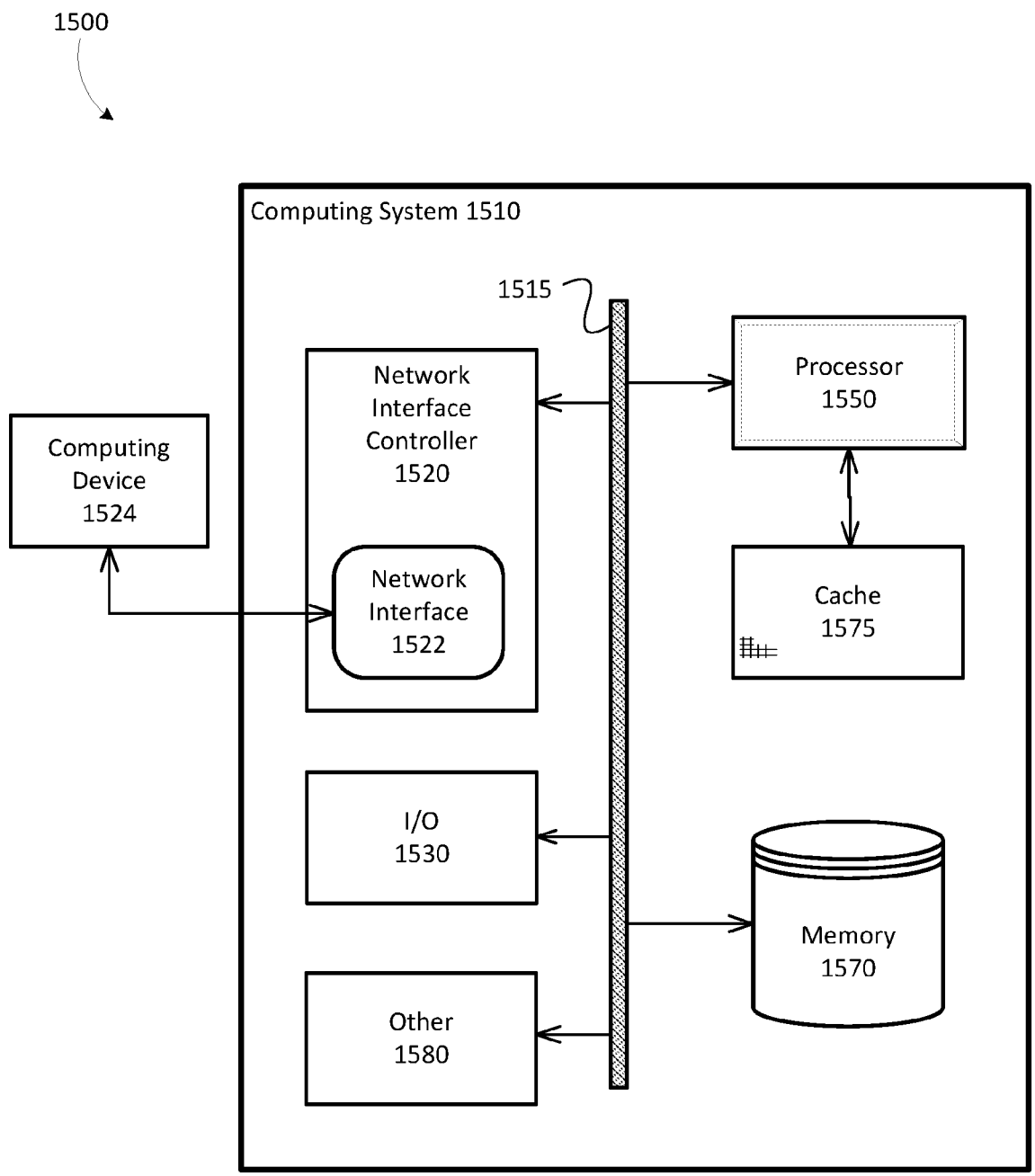
FIG. 7 illustrates a block diagram of an example computing system.

FIG. 7 illustrates a block diagram of an example computing system 1500. In some implementations, the computing system 1500 may be utilized in implementing the diagnostic system methods in FIGS. 3-6 below.

In broad overview, the computing system 1510 includes at least one processor 1550 for performing actions in accordance with instructions and one or more memory devices 1570 or 1575 for storing instructions and data. The illustrated example computing system 1510 includes one or more processors 1550 in communication, via a bus 1515, with at least one network interface controller 1520 with network interface ports 1522(a-n) connecting to other computing devices 1524(a-n), memory 1570, and any other devices 1580, e.g., an I/O interface. Generally, a processor 1550 will execute instructions received from memory. The processor 1550 illustrated incorporates, or is directly connected to, cache memory 1575.

In more detail, the processor 1550 may be any logic circuitry that processes instructions, e.g., instructions fetched from the memory 1570 or cache 1575. In many embodiments, the processor 1550 is a microprocessor unit or special purpose processor. The computing device 1500 may be based on any processor, or set of processors, capable of operating as described herein. In some implementations, the processor 1550 can be capable of executing the diagnostic system methods shown in FIGS. 4-6. The processor 1550 may be a single core or multi-core processor. The processor 1550 may be multiple processors. In some implementations, the processor 1550 can be configured to run multi-threaded operations. In some implementations, the processor 1550 may host one or more virtual machines or containers, along with a hypervisor or container manager for managing the operation of the virtual machines or containers. In such implementations, one or more of the methods 1300 and 1400 shown in FIGS. 4-6 can be implemented within the virtualized or containerized environments provided on the processor 1550.

The memory 1570 may be any device suitable for storing computer readable data. The memory 1570 may be a device with fixed storage or a device for reading removable storage media. Examples include all forms of non-volatile memory, media and memory devices, semiconductor memory devices (e.g., EPROM, EEPROM, SDRAM, and flash memory devices), magnetic disks, magneto optical disks, and optical discs (e.g., CD ROM, DVD-ROM, and BluRay® discs). A computing system 1500 may have any number of memory devices 1570. In some implementations, the memory 1570 can include instructions corresponding to the Internet notification methods 1300 and 1400 shown in FIGS. 3 and 4. In some implementations, the memory 1570 supports virtualized or containerized memory accessible by virtual machine or container execution environments provided by the computing system 1510.

The cache memory 1575 is generally a form of computer memory placed in close proximity to the processor 1550 for fast read times. In some implementations, the cache memory 1575 is part of, or on the same chip as, the processor 1550. In some implementations, there are multiple levels of cache 1575, e.g., L2 and L3 cache layers.

The network interface controller 1520 manages data exchanges via the network interfaces 1522(a-n) (also referred to as network interface ports). The network interface controller 1520 handles the physical and data link layers of the OSI model for network communication. In some implementations, some of the network interface controller's tasks are handled by the processor 1550. In some implementations, the network interface controller 1520 is part of the processor 1550. In some implementations, a computing system 1510 has multiple network interface controllers 1520. The network interfaces 1522(a-n) are connection points for physical network links. In some implementations, the network interface controller 1520 supports wireless network connections and an interface port 1522 is a wireless receiver/transmitter. Generally, a computing device 1510 exchanges data with other computing devices 1512(a-n) via physical or wireless links to a network interfaces 1522(a-n). In some implementations, the network interface controller 1520 implements a network protocol such as Ethernet.

The other computing devices 1524(a-n) are connected to the computing device 1510 via a network interface port 1522. The other computing devices 1524(a-n) may be peer computing devices, network devices, or any other computing device with network functionality. For example, a first computing device 1524(a) may be a network device such as a hub, a bridge, a switch, or a router, connecting the computing device 1510 to a data network such as the Internet.

The other devices 1580 may include an I/O interface, external serial device ports, and any additional co-processors. For example, a computing system 1510 may include an interface (e.g., a universal serial bus (USB) interface) for connecting input devices (e.g., a keyboard, microphone, mouse, or other pointing device), output devices (e.g., video display, speaker, or printer), or additional memory devices (e.g., portable flash drive or external media drive). In some implementations, a computing device 1500 includes an additional device 1580 such as a coprocessor, e.g., a math co-processor can assist the processor 1550 with high precision or complex calculations.

Referring back to FIG. 1, FIG. 3 illustrates a flow chart of an example method for identifying depression biotypes in a subject and predicting a treatment prognosis. The method 1000 includes performing fMRI on a subject (step 1001). The diagnostic system 101 collects the fMRI signal (step 1002). After collecting the fMRI signal, the extraction module 103 within the neuroimaging processor 102 extracts the fMRI BOLD signal 108 (step 1003). The depression biotype classification module 104 receives the extracted fMRI BOLD signal 108 and classifies the subject into an identified depression biotype (step 1004). Additionally, the treatment prognosis classification module 105 receives the identified depression biotype and outputs a treatment prognosis 106 based on the subject's depression biotype 107 (step 1005).

At step 1001, the method 1000 includes performing a resting state fMRI on a subject with an fMRI machine 114. The fMRI machine 114 uses magnetic resonance imaging to map neural networks of a subject's brain and records in vivo a whole brain scan of an individual 115. The resting state fMRI is a method of functional brain imaging that evaluates the connectivity of a subject's brain while the subject is at rest. A resting state subject means that they are awake but not performing any specific task. In some implementations, the subject is laying down with his eyes closed. In some implementations, the subject is laying down with their eyes open. Resting state fMRI is especially useful because it can be easily utilized in diverse patient populations. Resting state fMRI can quantify functional connectivity in resting state brain networks in terms of correlated, spontaneous fluctuations in the MR signal, which are closely related to structural and synaptic measures of connectivity and which are unbiased by the subject performing a specific task.

At step 1002, the neuroimaging processor 102 collects the fMRI signal from the subject. In some implementations, a subject's resting state fMRI includes, but it is not limited to metabolic measures of neural activity mediated by a hemodynamic response. In some implementations, the fMRI signal is preprocessed to control for artifacts caused by the subject's breathing or cardiac pulsations. In some implementations, the fMRI signal is additionally or alternatively preprocessed to control for motion, age, and other scanner related effects in the data.

At step 1003, the neuroimaging processor 102 sends the fMRI signal to the extraction module 103 and the extraction module 103 extracts the fMRI BOLD signal 108 from the fMRI signal. The blood oxygen level dependent signal, or the BOLD signal, measures the increase in blood oxygenation caused by neuronal activity. The fMRI BOLD signal 108 is an indirect measure of neuronal activity. It reflects a function of neural activity, blood flow, and changes in blood volume in the brain. As neurons are stimulated in the brain, oxygenated blood flow increases in the activated region, thereby increasing blood volume. The fMRI BOLD signal 108 measures neural activity through blood oxygen levels.

In some implementation, the extracted fMRI BOLD signal 108 consists of a plurality of connectivity features. The connectivity features represent the large-scale spatial networks of the subject's brain. In some implementations, the extraction module 103 extracts the fMRI BOLD signal 108 after the functional volume of the fMRI data is resampled and co-registered to a common space. In some implementations, a parcellation system is applied to the fMRI data to delineate a plurality of functional networks nodes. In some implementations, the functional network nodes span most cortical, subcortical, and cerebellar areas of the brain. In some implementations, an fMRI BOLD signal residual time series is extracted for each functional node and correlation matrixes are calculated between these time series to obtain an unbiased estimate of the functional connectivity across the whole brain of each subject.

At step 1004, the depression biotype classification module 104 receives the extracted fMRI BOLD signal 108 from step 1003 and classifies the subject into an identified depression biotype 107. As described above, the classification results in an identified depression biotype. Also, as described above, the depression biotype includes one of at least four depression biotypes, Biotype 1, Biotype 2, Biotype 3, and Biotype 4. An identified depression biotype is based on patterns of abnormal connectivity in a subject's resting state brain networks. In some implementations, alterations in fronto-amygdala functional connectivity are most severe in Biotypes 1 and 4. In some implementations, the alterations in thalamic and frontostriatal hyerconnectivity are most severe in Biotypes 3 and 4. In some implementations, alterations in anterior cingulate and orbitofrontal functional connectivity are most severe in Biotypes 1 and 2.

In some implementations, a principal component representation is applied to the functional connectivity features in order to convert the functional connectivity features into linearly uncorrelated variables referred to as principal components. In some implementations, the principal component variables are used as an input for linear support vector machine classifiers to output the likelihood of an identified depression biotype. Details of a method for identifying depression biotypes and details on the alterations in functional connectivity between different brain regions for identifying depression biotypes are described further in relation to FIG. 4.

At step 1005, the treatment prognosis classification module 105 uses the depression biotype 107 from step 1004 as an input to classify a subject's likely response to an antidepressant treatment option. The likelihood that a subject will respond to antidepressant treatment is derived from the functional connectivity features extracted from the fMRI signal. In some implementations, a principal component analysis representation is applied to the functional connectivity features. In some implementations, a linear support vector machine classifier calculates a score corresponding to the likelihood of a subject responding to treatment. In some implementations, the antidepressant treatment option is rTMS. A more detailed discussion of methods for classifying a subject's response to a depression treatment option is described in relation to FIG. 5.

Figure 4:
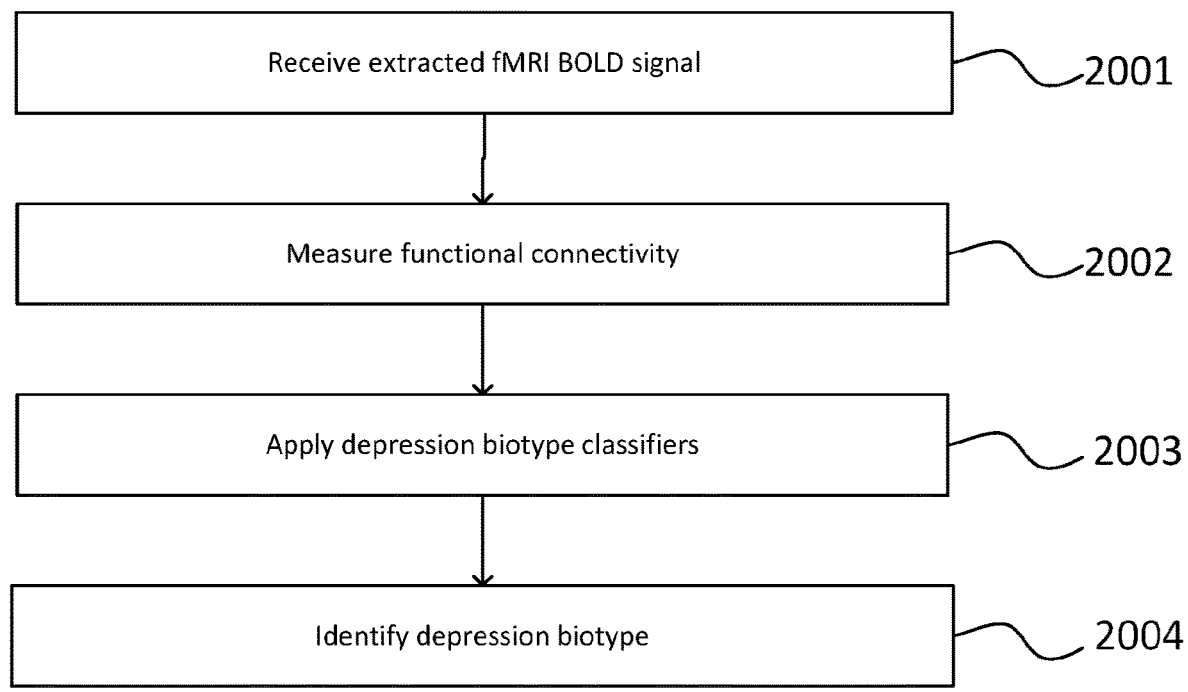
FIG. 4 illustrates a flow chart of an example method for identifying a depression biotype and predicting a treatment prognosis.

Referring to FIGS. 1 and 2, FIG. 4 illustrates a flow chart of an example method 2000 for classifying a depression biotype. The method 2000 includes the depression biotype classification module 104 receiving the extracted fMRI BOLD signal 108 from the neuroimaging processor 102 and extraction module 103 (step 2001). The depression biotype classification module measures the functional connectivity using the fMRI BOLD signal 108 from step 2001 (step 2002). Depression biotype classifiers are applied to the pairwise fMRI functional connectivity measures (step 2003). Based on the output of the depression biotype classifiers in step 2003, the subject is identified with a depression biotype (step 2004).

As set forth above, the method 2000 includes receiving the extracted fMRI BOLD signal 108 from the neuroimaging processor 102 and the extraction module 103. The extracted fMRI BOLD signal 108 represents the neural activity in the brain by measuring neural activity through blood oxygen levels.

After the fMRI BOLD signal 108 is extracted from the fMRI signal, the depression biotype classification module 104 measures the subject's functional connectivity (step 2002). In some implementations, the fMRI BOLD signal is extracted after the functional volume of the fMRI data is resampled and co-registered to a common space. In some implementations, a parcellation system may be used to delineate a plurality of functional network nodes spanning most cortical, subcortical, and cerebellar areas of the subject's brain. In some implementations, an fMRI BOLD signal residual time series is extracted from each of the plurality of network nodes and correlation matrixes are performed on these time series to obtain an unbiased estimate of the architecture of functional connectivity across the whole brain in a subject.

A depression biotype classification module 104 collects the subject's depression-related functional connectivity features and classifies the subject into an identified depression biotype (step 2003). As described above, the depression biotype includes one of at least four depression biotypes, Biotype 1, Biotype 2, Biotype 3, and Biotype 4. Each depression biotype relates to distinct patterns of abnormal functional connectivity in the brain. For example, in some implementations, alterations in fronto-amygdala functional connectivity are most severe in Biotypes 1 and 4, which are associated with increased anxiety. In contrast, thalamic and frontostriatal hyperconnectivity are pronounced in Biotype 3 and 4, which are associated with increased anhedonia and psychomotor retardation. Also, anterior cingulate and orbitofrontal connectivity alterations are pronounced in Biotypes 1 and 2, which are associated with increased anergia and fatigue. The depression biotype classifiers may be a linear support vector machine classifiers. The linear support vector machine classifiers are a previously trained machine learning algorithm. In a learning phase, or training phase, the depression biotype classifiers seeks to find a linear optimal hyperplane in order to maximize the separation between multiple classes or multiple biotypes and decipher patterns in the data. In a use phase, the depression biotype classifiers rely on the previously identified patterns to classify the subject into an identified depression biotype 107. In some implementations, the depression biotype classification module 104 may be comprised of four depression biotype classifiers to identify the depression biotype. In some implementations, the depression biotype classification module 104 may be comprised of eight depression biotype classifiers to identify the depression biotype.

The linear support vector machine classifiers identify the subject's depression biotype (step 2004). The linear support vector machine classifiers identify a depression biotype by outputting the likelihood of an identified depression biotype based on the pairwise fMRI functional connectivity measures between neuroanatomical brain regions, described in further detail below. An identified depression biotype is based on patterns of abnormal connectivity in resting state brain networks.

In some implementations, individuals with a known DSM (Diagnostic and Statistical Manual of Mental Disorder) diagnosis may be classified into one of the four depression biotypes Biotype 1, Biotype 2, Biotype 3, and Biotype 4. For example, when an individual has a known DSM diagnosis, the depression biotype classification module may be comprised of four depression biotype classifiers, one for each of the four depression biotypes. Each depression biotype classifier is a linear support vector machine classifier. Each of the four depression biotype classifiers calculates a score corresponding to the likelihood of a given individual fitting within its respective biotype. The depression biotype classification module 104 then assigns the individual to an identified depression biotype with the highest classifier score. The classifier scores derive from the pairwise fMRI functional connectivity measures between the following neuroanatomical brain regions including, dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex.

In some implementations, individuals with no known DSM diagnosis may be classified into one of the four depression biotypes. For example, when an individual has no known DSM diagnosis, the depression biotype classification module may be comprised of eight linear support vector machine classifiers. Four of the linear support vector machine classifiers correspond to each of the four depression biotypes and the remaining four linear support vector machine classifiers correspond to whether the individual is depressed or healthy. First, the depression biotype classification module 104 assigns the individual to an identified depression biotype based on their highest score from the four depression biotype classifiers. As mentioned above, the score for each of the biotype classifiers may be derived from pairwise fMRI functional connectivity measures between the following neuroanatomical brain regions including, dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex. Second, the depression biotype classification module 104 determines whether the individual belongs in that identified depression biotype or is not actively depressed, as described below.

In some implementations, the classifier determining whether the individual belongs in Biotype 1 or is not actively depressed may be derived from pairwise fMRI functional connectivity measures between the following neuroanatomical brain regions including, posterior parietal cortex, precuneus, middle temporal gyms, parahippocampal cortex, dorsolateral prefrontal cortex, ventrolateral prefrontal cortex, insular cortex, temporal pol, superior temporal gyms, ventromedial prefrontal cortex, ventral hippocampus, amygdala, ventral caudate nucleus, ventral striatum, thalamus, primary somatosensory cortex, primary motor cortex, visual cortex.

In some implementations, the classifier determining whether the individual belongs in Biotype 2 or is not actively depressed may be derived from pairwise fMRI functional connectivity measures between the following neuroanatomical brain regions including, dorsomedial prefrontal cortex, ventromedial prefrontal cortex, orbitofrontal cortex, posterior cingulate cortex, fusiform gyms, middle temporal gyms, parahippocampal cortex, anterior cingulate cortex, ventrolateral prefrontal cortex, dorsolateral prefrontal cortex, insular cortex, posterior parietal cortex, thalamus, primary somatosensory cortex, primary motor cortex, and visual cortex.

In some implementations, the classifier determining whether the individual belongs in Biotype 3 or is not actively depressed may be derived from pairwise fMRI functional connectivity measures between the following neuroanatomical brain regions including, ventromedial prefrontal cortex, posterior parietal cortex, middle temporal gyms, ventrolateral prefrontal cortex, anterior prefrontal cortex, dorsolateral prefrontal cortex, posterior parietal cortex, temporal pole, superior temporal gyms, orbitofrontal cortex, parahippocampal cortex, ventral hippocampus, amygdala, subgenual anterior cingulate cortex, ventral caudate nucleus, ventral striatum, thalamus, premotor cortex, supplementary motor area, insular cortex, anterior cingulate cortex, fusiform gyrus.

In some implementations, the classifier determining whether the individual belongs in Biotype 4 or is not actively depressed may be derived from pairwise fMRI functional connectivity measures between the following neuroanatomical brain regions including, fusiform gyms, parahippocampal cortex, ventrolateral prefrontal cortex, posterior parietal cortex, anterior cingulate cortex, middle cingulate cortex, insular cortex, temporal pole, superior temporal gyms, middle temporal gyrus, orbitofrontal cortex, ventral hippocampus, subgenual anterior cingulate cortex, ventral striatum, thalamus, primary somatosensory cortex, supplementary motor area, insular cortex, postcentral gyrus, and lingual gyms.

In some implementations, the classifier score may be derived based on the pairwise fMRI functional connectivity measures of all of the above brain regions. In some implementations, the classifier score may be derived based on a subset of the pairwise fMRI functional connectivity measures of the above brain regions. In some implementations, the classifier may be based on pairwise fMRI functional connectivity measures between the above mentioned brain regions with additional brain regions or between pairs of other brain regions neither of which are mentioned above. In some implementations, the fMRI measures of functional connectivity are taken between the centroids of a pair of neuroanatomical brain regions. In some implementations, the fMRI measures of functional connectivity are taken between corresponding points within the vicinity of the respective neuroanatomical brain regions of a given pair of regions.

In some implementations, the score for each classifier may be derived from a low-dimensional principal component representation of the functional connectivity between the neuroanatomical brain regions listed above, plus a patient's clinical symptoms. The principal component analysis representation is a decomposition method used to reduce the dimensionality of data. The principal component analysis representation of the subject's functional connectivity features reduces the number of features used to represent the data by applying an orthogonal transformation to convert the functional connectivity features into a set of linearly correlated variables called principal components. The number of principal components is less than the number of functional connectivity features. As would be known to a person having ordinary skill in the art, principal component analysis representation is frequently used for data compression and feature selection. The patient's clinical symptoms may be represented by either a self-reported clinical symptom rating such as the patient's item-level responses to the 21-item Beck Depression Inventory, or clinician rating of clinical symptom severity such as the patient's item-level responses to the 17-item Hamilton Depression Rating Scale ("Ham-D").

Figure 5:
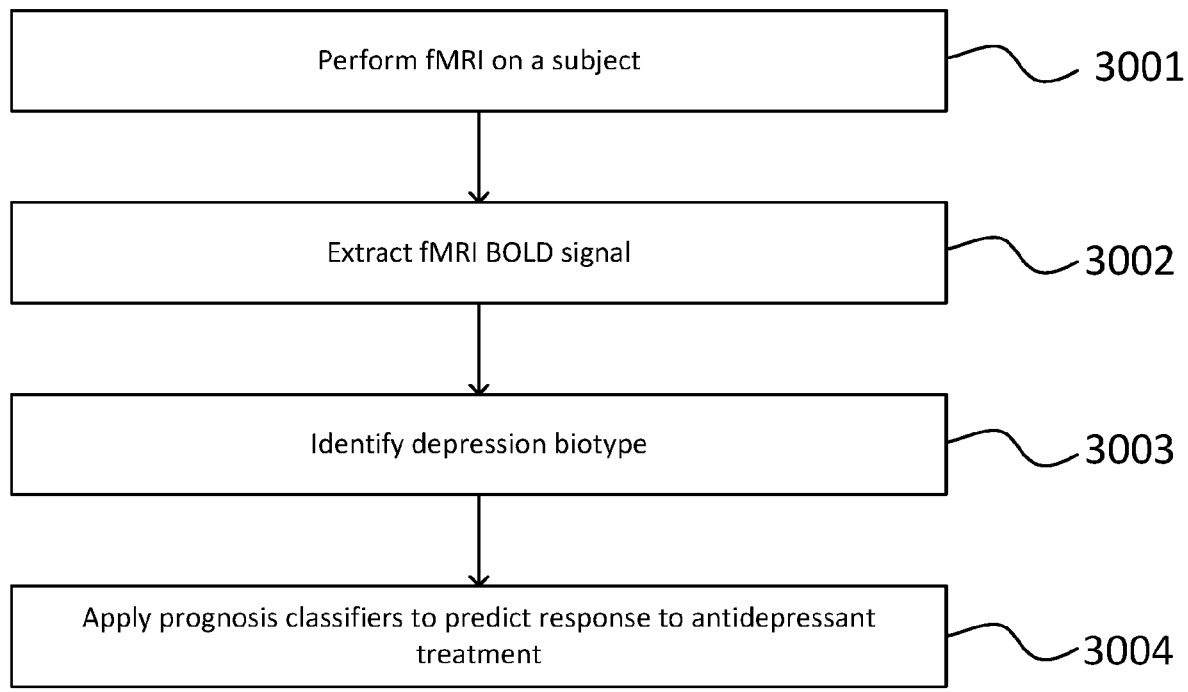
FIG. 5 illustrates a flow chart of an example method for identifying a subject's response to a depression treatment option.

Referring to FIG. 2, FIG. 5 illustrates a flow chart of an example method 3000 for classifying a subject's likely treatment response based on their identified depression biotype. The treatment prognosis classification module 109 identifies the treatment prognosis 106 based on the connectivity features and the clinical symptom profile to differentiate treatment responders from non-responders. It outputs the likelihood that the subject will respond to an antidepressant treatment. The method 3000 includes performing fMRI imaging on a subject by using an fMRI machine 114 (step 3001). The fMRI BOLD signal 108 is extracted from the fMRI data (step 3002) and the depression biotype is identified (step 3003). The treatment prognosis classification module 109 predicts the subject's antidepressant response to treatment based on the subject's pairwise fMRI functional connectivity measures (step 3004).

As set forth above, the method 3000 includes performing a resting state fMRI on a subject through an fMRI machine 114 (step 3001). The step 3001 can be identical to step 1001 shown before.

A neuroimaging processor 102 collects the fMRI data from the subject and the extraction module 103 extracts the fMRI BOLD signal 108 (step 3002). As mentioned above, the fMRI BOLD signal is an indirect measurement of neural activity in the brain of the subject. The step 3002 can be identical to step 1003 shown before.

Next, the method 3000 includes identifying the individual's depression biotype (step 3003). As described above, the depression biotype includes one of at least four depression biotypes, Biotype 1, Biotype 2, Biotype 3, and Biotype 4. Each depression biotype relates to distinct patterns of abnormal functional connectivity in the brain. In step 3003, the treatment prognosis classification module 109 receives the fMRI BOLD signal 108 and identifies the individual's depression biotype. Similar to above, in some implementations, individuals with a known DSM (Diagnostic and Statistical Manual of Mental Disorder) diagnosis may be classified into one of the four depression biotypes. For example, when an individual has a known DSM diagnosis, the treatment prognosis classification module 109 may be comprised of four linear support vector machine classifiers, one for each of the four depression biotypes. Each of the four depression biotype classifiers calculates a score corresponding to the likelihood of a given individual fitting within each of the four biotypes. The treatment prognosis classification module 109 then assigns the individual to an identified depression biotype with the highest classifier score. In some implementations, each classifier score may be derived from pairwise fMRI functional connectivity measures between the following neuroanatomical brain regions including, dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex.

In some implementations, the treatment prognosis classification module 109 may classify individuals with no known DSM diagnosis into one of the four depression biotypes. For example, when an individual has no known DSM diagnosis, the treatment prognosis classification module 109 may be comprised of eight linear support vector machine classifiers. Four of the linear support vector machine classifiers correspond to each of the four depression biotypes and the remaining four linear support vector machine classifiers correspond to each of the four depression biotypes and whether the individual is actively depressed. First, the treatment prognosis classification module 109 assigns the individual to an identified depression biotype based on the highest score. As mentioned above, the score for each of the biotype classifiers may be derived from pairwise fMRI functional connectivity measures between the following neuroanatomical brain regions including, dorsomedial prefrontal cortex, middle temporal gyrus, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex. Second, the prognosis classification module 109 determines whether the individual belongs in that identified depression biotype or is not actively depressed, as described in the following four sections.

In some implementations, the classifier determining whether the individual belongs in Biotype 1 or is not actively depressed may be derived from pairwise fMRI functional connectivity measures between the following neuroanatomical brain regions including, posterior parietal cortex, precuneus, middle temporal gyrus, parahippocampal cortex, dorsolateral prefrontal cortex, ventrolateral prefrontal cortex, insular cortex, temporal pol, superior temporal gyrus, ventromedial prefrontal cortex, ventral hippocampus, amygdala, ventral caudate nucleus, ventral striatum, thalamus, primary somatosensory cortex, primary motor cortex, visual cortex.

In some implementations, the classifier determining whether the individual belongs in Biotype 2 or is not actively depressed may be derived from pairwise fMRI functional connectivity measures between the following neuroanatomical brain regions including, dorsomedial prefrontal cortex, ventromedial prefrontal cortex, orbitofrontal cortex, posterior cingulate cortex, fusiform gyrus, middle temporal gyrus, parahippocampal cortex, anterior cingulate cortex, ventrolateral prefrontal cortex, dorsolateral prefrontal cortex, insular cortex, posterior parietal cortex, thalamus, primary somatosensory cortex, primary motor cortex, and visual cortex.

In some implementations, the classifier determining whether the individual belongs in Biotype 3 or is not actively depressed may be derived from pairwise fMRI functional connectivity measures between the following neuroanatomical brain regions including, ventromedial prefrontal cortex, posterior parietal cortex, middle temporal gyms, parahippocampal cortex, ventrolateral prefrontal cortex, anterior prefrontal cortex, dorsolateral prefrontal cortex, posterior parietal cortex, temporal pole, superior temporal gyrus, orbitofrontal cortex, ventral hippocampus, amygdala, subgenual anterior cingulate cortex, ventral caudate nucleus, ventral striatum, thalamus, premotor cortex, supplementary motor area, insular cortex, anterior cingulate cortex, fusiform gyrus.

In some implementations, the classifier determining whether the individual belongs in Biotype 4 or is not depressed may be derived from pairwise fMRI functional connectivity measures between the following neuroanatomical brain regions including, fusiform gyms, parahippocampal cortex, ventrolateral prefrontal cortex, posterior parietal cortex, anterior cingulate cortex, middle cingulate cortex, insular cortex, temporal pole, superior temporal gyms, middle temporal gyms, orbitofrontal cortex, ventral hippocampus, subgenual anterior cingulate cortex, ventral striatum, thalamus, primary somatosensory cortex, supplementary motor area, insular cortex, postcentral gyrus, and lingual gyms.

Next, the treatment prognosis classifier outputs the likelihood that the subject will respond to an antidepressant treatment (step 3004). Similar to the depression biotype classifiers, the treatment prognosis classifier may be a linear support vector machine classifier. The linear support vector machine classifier is a previously trained machine learning algorithm. In the learning phase, or training phase, the treatment prognosis classifier seeks to find an optimal hyperplane in order to maximize the separation between multiple classes or treatment outcomes and decipher patterns in the data. In the use phase, the treatment prognosis classifier relies on the previously identified patterns to classify the subject into an identified treatment prognosis. The treatment prognosis classifier calculates a score corresponding to the likelihood that the individual will respond to antidepressant treatment. The score for the treatment prognosis classifier may be derived from the identified depression biotype of step 3003 and the pairwise fMRI functional connectivity measures. In some implementations, pairwise fMRI functional connectivity measures may be derived from the following neuroanatomical brain regions including, dorsomedial prefrontal cortex, anterior cingulate cortex, posterior cingulate cortex, ventromedial prefrontal cortex, ventrolateral prefrontal cortex, dorsolateral prefrontal cortex, posterior parietal cortex, orbitofrontal cortex, amygdala, ventral striatum, nucleus accumbens, globus pallidus, thalamus, primary motor cortex, primary somatosensory cortex, and visual cortex.

In some implementations, the classifier score may be derived based on the pairwise fMRI functional connectivity measures of all of the above brain regions. In some implementations, the classifier score may be derived based on a subset of the pairwise fMRI functional connectivity measures of the above brain regions. In some implementations, the classifier may be based on pairwise fMRI functional connectivity measures between the above mentioned brain regions with additional brain regions or between pairs of other brain regions neither of which are mentioned above. In some implementations, the fMRI measures of functional connectivity are taken between the centroids of a pair of neuroanatomical brain regions. In some implementations, the fMRI measures of functional connectivity are taken between corresponding points within the vicinity of the respective neuroanatomical brain regions of a given pair of regions.

In some implementations, the score from treatment prognosis classifier may be derived from a principal component representation. The principal component analysis representation is a decomposition method used to reduce the dimensionality of data. The principal component analysis representation of the functional connectivity features reduces the number of features used to represent the data. The score for the treatment prognosis classifier may be derived from the identified depression biotype from step 3003 and the principal component representation of the same fMRI measure of functional connectivity derived from the neuroanatomical brain regions listed above. In some implementations, the principal component representation of the subject's functional connectivity features in the treatment prognosis module also applies the subject's clinical symptom profile of depression. In some implementations, the clinical symptom profiles include a 17 item Ham-D clinician-administered depression assessment scale. In some implementations, the clinical symptom profile includes a 21 item Beck Depression Inventory self-reported depression assessment scale.

Testing for treatment response prediction is an important element of validating novel biomarkers and establishing their utility and potential for clinical actionability. In some implementations, the antidepressant treatment is a non-invasive neurostimulation treatment of rTMS targeting the dorsomedial prefrontal cortex for depression. rTMS is a non-invasive neurostimulation treatment for medication-resistant depression that acts by enhancing synaptic plasticity at the prefrontal stimulation target and modulating functional connectivity in cortical networks. In some implementations, efficacy of rTMS varies with functional connectivity measures. For example, the left dorsolateral prefrontal cortex is the most common target for stimulation, but efficacy also exists for a dorsomedial prefrontal cortical target. In some implementations, the dorsomedial prefrontal cortical area may be among some of the important neuroanatomical areas differentiating the four biotypes. Individual differences in the antidepressant response to rTMS may be predicted on the basis of the differences in functional connectivity and symptom profiles. In some implementations, patients in Biotype 1 were more than three times more likely to benefit from transcranial magnetic stimulation of the dorsomedial prefrontal cortex than those in Biotypes 2 or 4.

Referring to FIGS. 1 and 2, FIG. 6 illustrates a flow chart of an example method for predicting a subject's depression severity and tracking it over time. The severity module 120 quantifies the severity of a patient's depression based on the fMRI data instead of patient self-reports. The severity module 120 outputs the patient's depression severity to the severity tracker 121, which tracks the patient's change in depression severity over time. The method 4000 includes performing resting state fMRI imaging on a subject using an fMRI machine 114 (step 4001). The fMRI BOLD signal is extracted from the fMRI data (step 4002). The severity module 120 receives the fMRI BOLD signal from the neuroimaging processor 102 and predicts the subject's depression severity (step 4003). The severity module 120 outputs the subject's depression severity to the severity tracker and the severity tracker follows the subject's severity over time through multiple fMRI scans (step 4004).

As set forth above, the method 4000 includes performing a resting state fMRI on a subject through an fMRI machine 114 (step 4001). The fMRI machine uses magnetic resonance imaging to map neural networks of a subject's brain and records in vivo a whole brain scan of an individual. The resting state fMRI is a method of functional brain imaging that evaluates the connectivity of a subject's brain while the subject is at rest. The step 4001 can be identical to step 1001 shown above in FIG. 3.

A neuroimaging processor 102 collects the fMRI data from the subject and the extraction module 103 extracts the fMRI BOLD signal 108 (step 4002). As mentioned above, the fMRI BOLD signal is an indirect measurement of neural activity. The step 4002 can be identical to step 1003 shown above in FIG. 3.

The severity module 120 utilizes a multiple linear regression model to predict a subject's depression severity (step 4003). Multiple linear regression is a statistical method that studies the relationship between a response variable and multiple continuous, quantitative predictor variables. The response variable may be depression severity and the multiple continuous, quantitative predictor variables may be pairwise fMRI functional connectivity measures. In some implementations, the response variable may represent the actual depression severity of the subject, and the predictor variables may represent the pairwise fMRI functional connectivity measures. The multiple linear regression model models the relationship between multiple predictor variables and a response variable by fitting a linear equation to the observed data. The multiple linear regression model predicts depression severity by assigning weights to pairwise fMRI functional connectivity measures and summing across these weighted measures to yield a predicted depression severity score. The severity score positively correlates with a patient's depression severity. In some implementations, the multiple linear regression model utilizes pairwise fMRI functional connectivity measures between the following neuroanatomical brain regions including, dorsomedial prefrontal cortex, posterior cingulate cortex, precuneus, posterior parietal cortex, middle temporal gyrus, parahippocampal cortex, anterior prefrontal cortex, anterior cingulate cortex, ventrolateral prefrontal cortex, insular cortex, orbitofrontal cortex, ventral hippocampus, ventral striatum, thalamus, primary motor cortex, premotor cortex, and visual cortex. In some implementations, the severity module may include a low dimensional principal component representation of the pairwise fMRI functional connectivity measures.

In some implementations, the classifier score may be derived based on the pairwise fMRI functional connectivity measures of all of the above brain regions. In some implementations, the classifier score may be derived based on a subset of the pairwise fMRI functional connectivity measures of the above brain regions. In some implementations, the classifier may be based on pairwise fMRI functional connectivity measures between the above mentioned brain regions with additional brain regions or between pairs of other brain regions neither of which are mentioned above. In some implementations, the fMRI measures of functional connectivity are taken between the centroids of a pair of neuroanatomical brain regions. In some implementations, the fMRI measures of functional connectivity are taken between corresponding points within the vicinity of the respective neuroanatomical brain regions of a given pair of regions.

Next, the method 4000 includes outputting the subject's predicted depression severity score to the severity tracker 121. The severity tracker receives the subject's predicted depression severity score and stores the information. Over time and based on multiple resting state fMRI scans, the severity tracker compiles the subject's predicted severity depression scores. In comparison to evaluating depression severity based on answers to questionnaires, as is the typical practice currently, the fMRI-based severity depression scores are a more objective means to evaluate a subject's depression severity. For example, such scores are not susceptible to errors due to inconsistent interpretations of questionnaire questions or potential inaccurate or otherwise non-representative responses from subjects answering the questionnaires. In some implementations, the depression severity scores may be used for language or otherwise developmentally impaired or disabled subjects who may not be competent or capable of effectively responding to the questionnaires. In some implementations, the severity tracker 121 can determine if the subject's compilation of predicted severity scores increased or decreased, which determines whether the subject's depression severity has increased or decreased over time. In some implementation, the severity tracker 121 can determine the antidepressant treatment effectiveness based on changes over time in the subject's compilation of predicted severity scores. In some implementations, the severity tracker 121 can track the depression severity scores across multiple subjects having been identified as having the same depression biotype and receiving the same treatment, for example in the context of a clinical trial, to assess the effectiveness of the clinical trial.

EXPERIMENTAL RESULTS

To support the techniques described above, experiments were conducted to identify parameters that are particularly effective to determine depression biotypes and facilitate biotype classification. The biotype cluster discovery data was collected from 220 patients. To ensure that the cluster discovery was not confounded by site-related differences in subject recruitment criteria or other undefined variables, the cluster discovery analysis was conducted on these 220 patients who were recruited from two sites, with identical inclusion and exclusion criteria and statistically equivalent depression symptom scores.

The subjects underwent an fMRI scan of their brain. The data was processed to control for motion, age, and other scanner related effects. After resampling and co-registering the functional volumes to common space, a parcellation system was applied to the fMRI data to delineate 258 functional network nodes. Next, the fMRI BOLD signal residual time series was extracted for each functional node and correlation matrixes were calculated between these time series to obtain an unbiased estimate of the architecture of functional connectivity across the whole brain.

Each correlation matrix comprised about 33,000 unique connectivity features. To select a subset of connectivity features, the processor applied a canonical correlation analysis associated with weighted combinations of clinical symptoms, as quantified by the 17 item Ham-D scale, to the extracted fMRI BOLD signal data. The analysis revealed linear combinations of connectivity features (analogous to principal components) that predicted two distinct sets of depressive symptoms.

The first connectivity feature defined a combination of predominantly frontostriatal and orbitofrontal connectivity features that were correlated with anhedonia and psychomotor retardation. The second connectivity feature defined a distinct set of predominantly limbic connectivity features involving the amygdala, ventral hippocampus, ventral striatum, subgenual cingulate, and later prefrontal control areas and correlated with anxiety and insomnia. Hierarchical clustering revealed four depression biotypes defined by distinct and relatively homogenous patterns of connectivity along these two connectivity components. Additional potential clustering solutions were also evident within these four groups. In some implementations, the hierarchical cluster analysis uses Ward's minimum variance method.

After applying Wilcoxon rank sum tests and Kruskal Wallis ANOVA to the connectivity features of each biotype, two themes were revealed. First, a common neuroanatomical core of pathology underlying all four biotypes existed, which spanned the insula, orbitofrontal cortex, ventromedial prefrontal cortex, and multiple subcortical areas. The common neuroanatomical core predicted the severity of three "core" symptoms (depressed mood, anhedonia, fatigue) that were present in almost all patients, greater than 93.9%. Across all subjects, regardless of biotype, abnormal connectivity in the shared neuroanatomical core was significantly correlated with the three "core" depression symptoms between r=0.72 and r=0.82.

Also, distinct patterns of abnormal functional connectivity differentiated the four biotypes and were associated with specific clinical symptom profiles. For example, alterations in fronto-amygdala functional connectivity were most severe in Biotypes 1 and 4, which were associated with increased anxiety, a finding consistent with known roles for these projections in regulating fear-related behavior and reappraising the affective salience of negative emotional stimuli. In contrast, thalamic and frontostriatal hyperconnectivity were especially pronounced in Biotypes 3 and 4, and were associated with increased anhedonia and psychomotor retardation, in accord with posited roles for these projections in reward processing, adaptive motor control, and initiating movements. Anterior cingulate and orbitofrontal connectivity alterations were most severe in Biotypes 1 and 2, and were associated with increased anergia and fatigue, consistent with the role of these circuits in motivation and incentive salience assessments, respectively. These findings delineate clinically meaningful, homogeneous biotypes of depression with robust neurobiological correlates defined by distinct patterns of abnormal functional connectivity in frontostriatal and limbic networks, superimposed on one shared core pathology.

For developing classifiers for diagnosing depression biotypes based on pairwise fMRI functional connectivity measures, the classification process was optimized in a training dataset comprising 333 patients and 378 healthy controls matched for age and sex. The classifiers were trained iteratively on a randomly selected subset of these subjects, and then tested on an independent subset left out of all aspects of the training process. Support vector machine classifiers yielded overall accuracy rates of up to 89.2% based on connectivity features with the neuroanatomical areas, listed above in FIG. 4. In some implementations, the pairwise fMRI functional connectivity measures may include dorsomedial prefrontal cortex, middle temporal gyms, parahippocampal cortex, dorsolateral prefrontal cortex, anterior prefrontal cortex, posterior parietal cortex, anterior cingulate cortex, insular cortex, ventrolateral prefrontal cortex, precuneus, orbitofrontal cortex, ventral striatum thalamus, raphe nucleus (midbrain), primary cortex, somatosensory cortex, and visual cortex. In some implementations, the pairwise fMRI functional connectivity measures may include posterior parietal cortex, precuneus, middle temporal gyrus, parahippocampal cortex, dorsolateral prefrontal cortex, ventrolateral prefrontal cortex, insular cortex, temporal pol, superior temporal gyms, ventromedial prefrontal cortex, ventral hippocampus, amygdala, ventral caudate nucleus, ventral striatum, thalamus, primary somatosensory cortex, primary motor cortex, visual cortex. In some implementations, the pairwise fMRI functional connectivity features may include dorsomedial prefrontal cortex, ventromedial prefrontal cortex, orbitofrontal cortex, posterior cingulate cortex, fusiform gyrus, middle temporal gyrus, parahippocampal cortex, anterior cingulate cortex, ventrolateral prefrontal cortex, dorsolateral prefrontal cortex, insular cortex, posterior parietal cortex, thalamus, primary somatosensory cortex, primary motor cortex, and visual cortex. In some implementations, the pairwise fMRI functional connectivity measures may include ventromedial prefrontal cortex, posterior parietal cortex, middle temporal gyrus, ventrolateral prefrontal cortex, anterior prefrontal cortex, dorsolateral prefrontal cortex, posterior parietal cortex, temporal pole, superior temporal gyms, orbitofrontal cortex, parahippocampal cortex, ventral hippocampus, amygdala, subgenual anterior cingulate cortex, ventral caudate nucleus, ventral striatum, thalamus, premotor cortex, supplementary motor area, insular cortex, anterior cingulate cortex, fusiform gyrus. In some implementations, the pairwise fMRI functional connectivity measures may include fusiform gyrus, parahippocampal cortex, ventrolateral prefrontal cortex, posterior parietal cortex, anterior cingulate cortex, middle cingulate cortex, insular cortex, temporal pole, superior temporal gyms, middle temporal gyms, orbitofrontal cortex, ventral hippocampus, subgenual anterior cingulate cortex, ventral striatum, thalamus, primary somatosensory cortex, supplementary motor area, insular cortex, postcentral gyrus, and lingual gyms.

For further biotype validation, the classifiers were tested on a subset of patients, N=50, who received a second fMRI scan wile actively depressed, 4-6 weeks after the first scanning session. The results showed that 90% of subjects were assigned to the same biotype in both scans, $\chi2$=84.6, p<0.0001, including 92.3% and 93.3% of subjects in Biotypes 2 and 3. Tests were also conducted to determine whether the clustering results were influenced by differences in other variables that have known or suspected effects on resting state fMRI measures of functional connectivity, including age, medication usage, and head motion during scanning Results showed no significant between group differences on any of these measures.

To ensure that the classifier performance was not an overestimation based on iterative training and cross-validation on the same data, further tests were conducted. The most successful classifier for each biotype was tested on an independent replication dataset, comprising 125 patients and 352 healthy controls acquired from 13 sites, including 5 sites that were not included in the original training dataset. To avoid overestimating diagnostic sensitivity, only one classifier, the classifier for the best fitting biotype, was tested on each subject, using the same two-step process outlined in Paragraphs 45-49 above. Overall, 86.2% of subjects in this independent, out-of-sample replication dataset were correctly diagnosed, including more than 90% of patients in Biotypes 3 and 4. By implementing stricter data quality controls and by treating subjects with ambiguous classification outcomes as equivocal test results (i.e. the lowest absolute SVM classification scores), these accuracy rates increased to more than 95%. This finding suggests room for improved diagnostic performance for neuroimaging biomarkers in prospective datasets acquired using state-of-the-art technology, which has proven capable of delivering significant improvements in signal quality and stability.

To test whether biotype differences in dysfunctional connectivity at the dorsomedial prefrontal cortical target site may give rise to differing treatment outcomes, a total of 124 subjects received repetitive high-frequency stimulation of the dorsomedial prefrontal cortex for five weeks beginning shortly after their fMRI scan. Treatment response varied significantly with cluster membership ($\chi 2=25.7$, $p=1.1\times 10-5$). rTMS was most effective for patients in Biotype 1, 82.5% of whom (33 of 40 subjects) improved significantly after treatment (partial response=25+% decrease in severity by Ham-D), compared to 61.0% for Biotype 3 (25 of 41 subjects) and only 25.0% and 29.6% for Biotypes 2 (4 of 16 subjects) and 4 (8 of 27 subjects), respectively.

The classifiers were trained to differentiate responders and non-responders using the same approach to feature selection, training, and leave-one-out cross-validation as described above. This tested whether connectivity based biotypes could be used to predict treatment response more effectively than clinical symptoms alone. The most discriminating functional connectivity features involved the dorsomedial prefrontal stimulation target and the left amygdala, left dorsolateral prefrontal cortex, bilateral orbitofrontal cortex, and posterior cingulate cortex. Connectivity between other neuroanatomical areas that were not directly stimulated by the rTMS protocol—including the ventromedial prefrontal cortex, thalamus, nucleus accumbens, and globus pallidus—was also highly associated with subsequent treatment response. Individual differences in the antidepressant response to rTMS could be predicted on the basis of these differences in functional connectivity with 78.3% accuracy in leave-one-out cross-validation analysis. Biotype diagnosis significantly improved classifier performance. Classification based on the same discriminating connectivity features plus biotype diagnosis increased overall accuracy rates to 89.6%, with a 93.6% correct prediction rate for non-responders, $p<0.001$. Accuracy rates could be further improved from 89.6% to >94% by implementing stricter data quality controls and treating subjects with ambiguous classification outcomes as equivocal test results.

In contrast, clinical symptoms alone were not strong predictors of rTMS treatment responsiveness at an individual level. To test this, classifiers were trained to differentiate responders and non-responders based solely on clinical data. The clinical features alone using Ham-D item-level responses were only modestly predictive of treatment responsiveness with 62.6% overall accuracy.

To further evaluate predictive validity, the best performing classifier, which utilized a combination of connectivity features and biotype diagnosis, was tested in an independent replication set, $N=30$ subjects, and obtained comparable accuracy rates: 87.5% for all subjects and 92.6% for subjects with high data quality and unequivocal predicted outcomes Supplementary analyses provide additional evidence that clinical symptom measures alone cannot substitute for resting state fMRI measures: subtyping subjects based on clinical symptoms yielded highly variable, longitudinally unstable clustering outcomes that also failed to predict treatment response. These results provide strong convergent evidence that a data-driven approach to clustering patients based on functional connectivity measures revealed biologically meaningful biotypes of depression with robust neurobiological correlates and strong predictive validity for a neurostimulatory antidepressant targeting dysfunction in the dorsomedial prefrontal cortical area.

To test whether a subject's depression severity can be determined based on brain region functional connectivity measures, a multiple linear regression model was fit to a sample of $N=497$ patients with major depressive disorder. A clinician-rated clinical symptom severity using the 17-item Ham-D depression scale scored patient severity. The score in this sample ($N=497$) ranged from 4, i.e., patients in full remission, to 38, i.e., patients with severe depression. The mean Ham-D score was 22.5 and the standard deviation was 5.2. A multiple linear regression model predicted a subject's depression severity by assigning weights to pairwise fMRI functional connectivity measures and summing across these weighted measures to yield a predicted depression severity. The multiple linear regression model utilized pairwise fMRI functional connectivity measures between the following neuroanatomical brain regions including, dorsomedial prefrontal cortex, posterior cingulate cortex, precuneus, posterior parietal cortex, middle temporal gyms, parahippocampal cortex, anterior prefrontal cortex, anterior cingulate cortex, ventrolateral prefrontal cortex, insular cortex, orbitofrontal cortex, ventral hippocampus, ventral striatum, thalamus, primary motor cortex, premotor cortex, and visual cortex. The method enabled accurate prediction of depression severity (root mean squared error=4.2 Ham-D points) based on brain region functional connectivity features, accounting for 48.5% of the variance in depression severity in the sample of $N=497$ depressed patients.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs embodied on a tangible medium, i.e., one or more modules of computer program instructions, encoded on one or more computer storage media for execution by, or to control the operation of, a data processing apparatus. A computer storage medium can be, or be included in, a computer-readable storage device, a computer-readable storage substrate, a random or serial access memory array or device, or a combination of one or more of them. The computer storage medium can also be, or be included in, one or more separate components or media (e.g., multiple CDs, disks, or other storage devices). The computer storage medium may be tangible and non-transitory.

The operations described in this specification can be implemented as operations performed by a data processing apparatus on data stored on one or more computer-readable storage devices or received from other sources. The operations may be executed within the native environment of the data processing apparatus or within one or more virtual machines or containers hosted by the data processing apparatus.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers or one or more virtual machines or containers that are located at one site or distributed across multiple sites and interconnected by a communication network. Examples of communication networks include a local area network ("LAN") and a wide area network ("WAN"), an internetwork (e.g., the Internet), and peer-to-peer networks (e.g., ad hoc peer-to-peer networks).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

What is claimed is:

1. A method for identifying a neurophysiological depression biotype in the brain of a patient, comprising:
   receiving, by a processor, functional magnetic resonance imaging (fMRI) data indicative of brain activity of the patient;
   extracting, by the processor, brain region functional connectivity information from the fMRI data,
      wherein the brain region functional connectivity information includes functional connectivity levels of a plurality of brain regions in the patient and
      wherein the plurality of brain regions includes the dorsomedial prefrontal cortex, the thalamus, the orbitofrontal cortex, and the anterior cingulate cortex;
   identifying the neurophysiological depression biotype from a plurality of neurophysiological depression biotypes for the patient by applying at least one support vector machine-based biotype classifier executing on the processor to the brain region functional connectivity information extracted from the fMRI data,
      wherein each of the plurality of neurophysiological depression biotypes corresponds to a different pattern of abnormal functional connectivity in the brain; and outputting, by the processor, the identified neurophysiological depression biotype.

2. The method of claim 1, wherein:
   the at least one support vector machine-based biotype classifier comprises a plurality of classifiers;
   the plurality of classifiers comprises a first set of classifiers, each classifier of the first set of classifiers configured to generate a biotype depression likelihood score for a different corresponding neurophysiological depression biotype; and
   the neurophysiological depression biotype is identified by selecting the neurophysiological depression biotype associated with the classifier of the first set of classifiers that generates the highest biotype depression likelihood score based on the extracted brain region functional connectivity information.

3. The method of claim 2, further comprising processing the extracted brain functional connectivity information by an additional classifier included in a second set of classifiers configured for determining if the patient suffers from the neurophysiological depression biotype identified for the patient, wherein the additional classifier is associated with the neurophysiological depression biotype identified for the patient.

4. The method of claim 3, further comprising:
   determining if the patient suffers from a first neurophysiological biotype of depression by processing the extracted brain region functional connectivity information between a plurality of the following patient's brain regions: the posterior parietal cortex, the precuneus, the middle temporal gyrus, the parahippocampal cortex, the dorsolateral prefrontal cortex, the ventrolateral prefrontal cortex, the insular cortex, the temporal pol, the superior temporal gyrus, the ventromedial prefrontal cortex, the ventral hippocampus, the amygdala, the ventral caudate nucleus, the ventral striatum, the thalamus, the primary somatosensory cortex, the primary motor cortex, the visual cortex,
      wherein the extracted brain region functional connectivity information is derived from pairwise fMRI functional connectivity measurements.

5. The method of claim 3, further comprising:
   determining if the patient suffers from a second biotype by processing the extracted brain region functional connectivity information between a plurality of the following patient brain regions: the dorsomedial prefrontal cortex, the ventromedial prefrontal cortex, the orbitofrontal cortex, the posterior cingulate cortex, the fusiform gyrus, the middle temporal gyrus, the parahippocampal cortex, the anterior cingulate cortex, the ventrolateral prefrontal cortex, the dorsolateral prefrontal cortex, the insular cortex, the posterior parietal cortex, the thalamus, the primary somatosensory cortex, the primary motor cortex, and the visual cortex,
  wherein the extracted brain region functional connectivity information is derived from pairwise fMRI functional connectivity measurements.

6. The method of claim 3, further comprising:
determining if the patient suffers from a third neurophysiological biotype by processing the extracted brain region functional connectivity information between a plurality of the following patient brain regions: the ventromedial prefrontal cortex, the posterior parietal cortex, the middle temporal gyrus, the parahippocampal cortex, the ventrolateral prefrontal cortex, the anterior prefrontal cortex, the dorsolateral prefrontal cortex, the posterior parietal cortex, the temporal pole, the superior temporal gyrus, the orbitofrontal cortex, the ventral hippocampus, the amygdala, the subgenual anterior cingulate cortex, the ventral caudate nucleus, the ventral striatum, the thalamus, the premotor cortex, the supplementary motor area, the insular cortex, the anterior cingulate cortex, and the fusiform gyrus,
  wherein the extracted brain region functional connectivity information is derived from pairwise fMRI functional connectivity measurements.

7. The method of claim 3, further comprising:
determining if the patient suffers from a fourth neurophysiological biotype by processing the extracted brain region functional connectivity information between a plurality of the following patient brain regions: the fusiform gyrus, the parahippocampal cortex, the ventrolateral prefrontal cortex, the posterior parietal cortex, the anterior cingulate cortex, the middle cingulate cortex, the insular cortex, the temporal pole, the superior temporal gyrus, the middle temporal gyrus, the orbitofrontal cortex, the ventral hippocampus, the subgenual anterior cingulate cortex, the ventral striatum, the thalamus, the primary somatosensory cortex, the supplementary motor area, the insular cortex, the postcentral gyrus, and the lingual gyrus,
  wherein the extracted brain region functional connectivity information is derived from pairwise fMRI functional connectivity measurements.

8. The method of claim 1, wherein identifying the neurophysiological depression biotype comprises performing a principal component analysis of the extracted brain region functional connectivity information.

9. The method of claim 1, wherein the at least one support vector machine-based biotype classifier comprises a linear support vector machine classifier configured to output the likelihood of an associated neurophysiological depression biotype.

10. The method of claim 1, further comprising classifying a depression treatment prognosis for the patient by applying a prognosis classifier to the extracted brain region functional connectivity information, wherein the prognosis classifier is configured to output a likelihood of success of an identified depression treatment for the patient.

11. The method of claim 10, wherein identifying the likelihood of success of the identified depression treatment for the patient comprises processing the extracted brain region functional connectivity information of the plurality of patient brain regions: the dorsomedial prefrontal cortex, the anterior cingulate cortex, the posterior cingulate cortex, the ventromedial prefrontal cortex, the ventrolateral prefrontal cortex, the dorsolateral prefrontal cortex, the posterior parietal cortex, the orbitofrontal cortex, the amygdala, the ventral striatum, the nucleus accumbens, the globus pallidus, the thalamus, the primary motor cortex, the primary somatosensory cortex, and the visual cortex.

12. The method of claim 11, wherein identifying the likelihood of success of the identified depression treatment for the patient comprises a principal component analysis of the extracted brain region functional connectivity.

13. The method of claim 11, wherein the identified depression treatment is a repetitive transcranial magnetic stimulation.

14. The method of claim 10, wherein the prognosis classifier comprises the at least one support vector machine-based classifier.

15. The method of claim 1, further comprising predicting a depression severity of the patient by processing the extracted brain region functional connectivity information with a multiple linear regression model.

16. The method of claim 15, wherein predicting the depression severity for a patient comprises processing the extracted brain region functional connectivity information of a plurality of the following patient brain regions: the dorsomedial prefrontal cortex, the posterior cingulate cortex, the precuneus, the posterior parietal cortex, the middle temporal gyrus, the parahippocampal cortex, the anterior prefrontal cortex, the anterior cingulate cortex, the ventrolateral prefrontal cortex, the insular cortex, the orbitofrontal cortex, the ventral hippocampus, the ventral striatum, the thalamus, the primary motor cortex, the premotor cortex, and the visual cortex.

17. A system for identifying neurophysiological depression biotypes in the brain of a patient, comprising;
  an input module configured to receive functional magnetic resonance imaging (fMRI) data from an fMRI scan;
  a connectivity evaluation module configured to process the received fMRI data to extract brain region functional connectivity information associated with a brain of the patient,
    wherein the brain region functional connectivity information includes functional connectivity levels of a plurality of brain regions in the patient and
    wherein the plurality of brain regions includes the dorsomedial prefrontal cortex, the thalamus, the orbitofrontal cortex, and the anterior cingulate cortex;
  a support vector machine-based biotype classification module configured to classify the patient into one of a plurality of neurophysiological depression biotypes,
    wherein each of the plurality of neurophysiological depression biotypes corresponds to a different pattern of abnormal functional connectivity in the brain; and
  an output module for outputting the neurophysiological depression biotype into which the patient was classified.

18. The system of claim 17, further comprising an fMRI machine coupled to the input module.

19. The system of claim 17, further comprising a depression severity predictor configured to predict a depression severity of the patient by processing the extracted brain region functional connectivity information with a multiple linear regression model.

20. The system of claim 19, wherein the depression severity predictor is configured to predict the depression severity for a patient by processing the extracted brain region functional connectivity information of a plurality of the following patient brain regions: the dorsomedial prefrontal cortex, the posterior cingulate cortex, the precuneus, the posterior parietal cortex, the middle temporal gyms, the parahippocampal cortex, the anterior prefrontal cortex, the anterior cingulate cortex, the ventrolateral prefrontal cortex, the insular cortex, the orbitofrontal cortex, the ventral hippocam pus, the ventral striatum, the thalamus, the primary motor cortex, the premotor cortex, and the visual cortex.

21. A non-transitory computer readable medium storing a computer readable instructions, which when executed by a processor cause the processor to carry out a method for identifying a neurophysiological depression biotype, the method comprising:

receiving, by the processor, functional magnetic resonance imaging (fMRI) data indicative of brain activity of a patient; extracting, by the processor, brain region functional connectivity information from the fMRI data, wherein the brain region functional connectivity information includes functional connectivity levels of a plurality of brain regions in the patient and
   wherein the plurality of brain regions includes the dorsomedial prefrontal cortex, the thalamus, the orbitofrontal cortex, and the anterior cingulate cortex;
  identifying a neurophysiological depression biotype from a plurality of depression biotypes for the patient by applying at least one support vector machine-based biotype classifier executing on the processor to the brain region functional connectivity information extracted from the fMRI data,
   wherein each of the plurality of depression biotypes corresponds to a different pattern of abnormal functional connectivity in the brain; and
  outputting, by the processor, the identified depression biotype.

* * * * *